United States Patent
Jones et al.

(10) Patent No.: US 8,882,721 B2
(45) Date of Patent: Nov. 11, 2014

(54) DRIVE ASSEMBLY SUITABLE FOR USE IN A DRUG DELIVERY DEVICE AND DRUG DELIVERY DEVICE

(75) Inventors: Matthew Meredith Jones, Warwick (GB); David Aubrey Plumptre, Droitwich (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 780 days.

(21) Appl. No.: 12/991,471

(22) PCT Filed: May 9, 2009

(86) PCT No.: PCT/EP2009/003310
§ 371 (c)(1),
(2), (4) Date: Feb. 28, 2011

(87) PCT Pub. No.: WO2009/141067
PCT Pub. Date: Nov. 26, 2009

(65) Prior Publication Data
US 2012/0010575 A1    Jan. 12, 2012

(30) Foreign Application Priority Data

May 20, 2008  (EP) ..................................... 08009260
Jun. 27, 2008  (EP) ..................................... 08011676

(51) Int. Cl.
*A61M 5/00* (2006.01)
*A61M 5/315* (2006.01)
*A61M 5/31* (2006.01)

(52) U.S. Cl.
CPC ....... *A61M 5/31593* (2013.01); *A61M 5/31551* (2013.01); *A61M 2005/3152* (2013.01); *A61M 5/31555* (2013.01); *A61M 2005/3126* (2013.01); *A61M 5/31541* (2013.01); *A61M 2005/3125* (2013.01)
USPC ......................................... 604/207; 604/186

(58) Field of Classification Search
CPC .................... A61M 5/31525; A61M 5/31533;
A61M 5/3155; A61M 5/13551; A61M 5/31555; A61M 5/31568; A61M 5/31593; A61M 5/31595; A61M 2005/3125; A61M 2005/3126
USPC ......................................... 604/186, 207–211
See application file for complete search history.

(56) References Cited

U.S. PATENT DOCUMENTS

2008/0051712 A1    2/2008  Fiechter et al.
2008/0108953 A1*   5/2008  Moser et al. .................. 604/224

FOREIGN PATENT DOCUMENTS

DE    102006038103    2/2008
WO    2007/067889     6/2007

OTHER PUBLICATIONS

European Search Report for corresponding European Patent Application No. EP 08009260 (2 pages), Dated Nov. 14, 2008.

(Continued)

*Primary Examiner* — Kami A Bosworth
(74) *Attorney, Agent, or Firm* — McDonnell Boehnen Hulbert & Berghoff LLP

(57) ABSTRACT

A drive assembly for use in a drug delivery device is proposed, the drive assembly comprising: a housing having a proximal end and a distal end; an axis extending between the proximal end and the distal end; at least one drive member; a piston rod adapted to be driven along the axis by the drive member; an indicator adapted to provide positional information about a position of the piston rod relative to the proximal end, wherein the indicator and the piston rod are configured to convert a movement of the piston rod with respect to the housing into a rotational movement of the indicator. Additionally, a drug delivery device comprising the drive assembly is provided for.

19 Claims, 16 Drawing Sheets

(56) References Cited

OTHER PUBLICATIONS

International Search Report for corresponding International Application No. PCT/EP2009/003310 (2 pages), Dated Jun. 15, 2009.

International Preliminary Report on Patentability for corresponding International Application No. PCT/EP2009/003310, Dated Dec. 2, 2010.

* cited by examiner

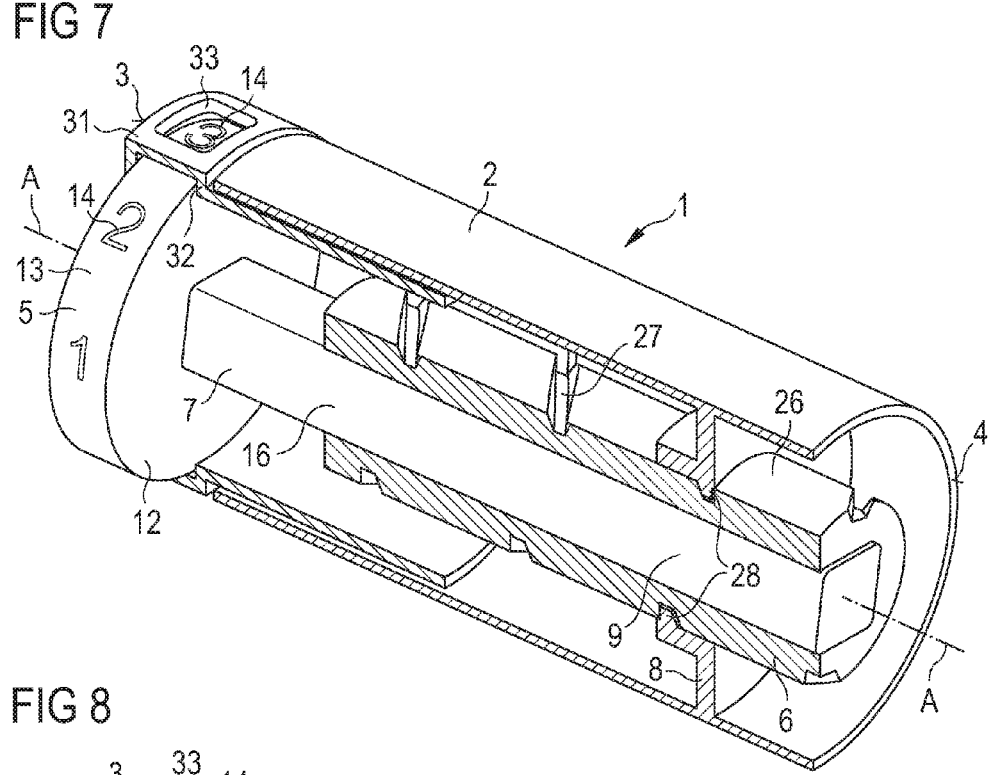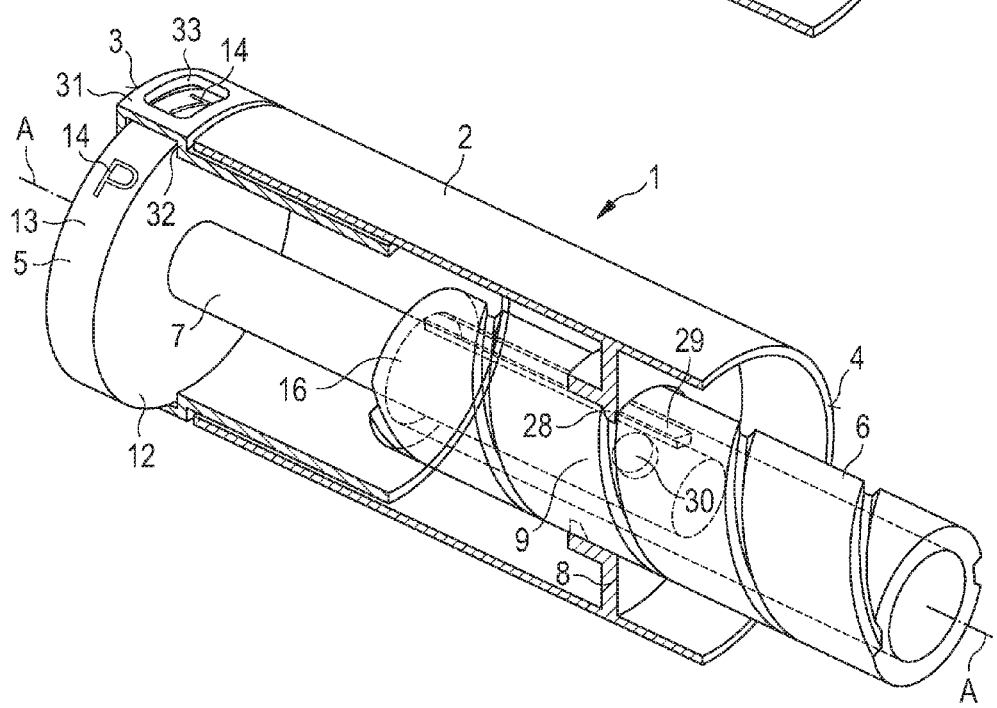

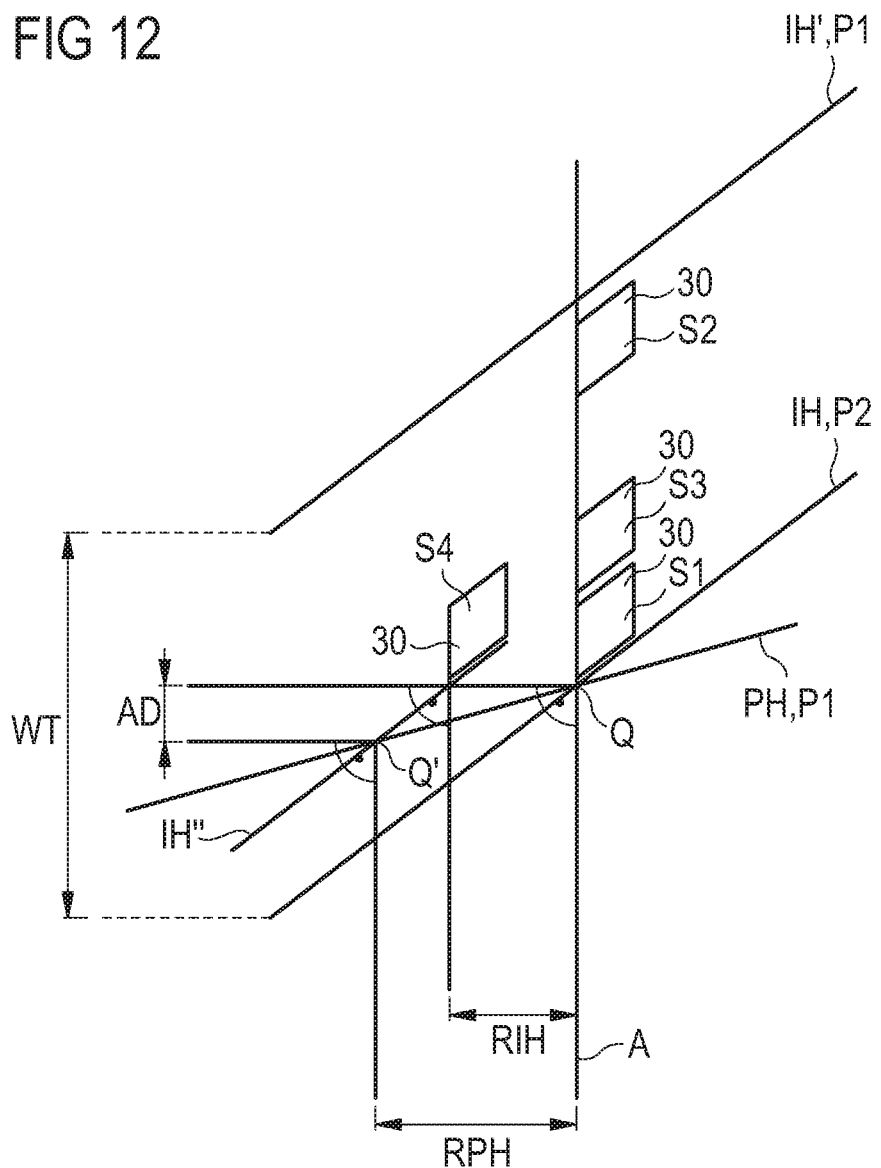

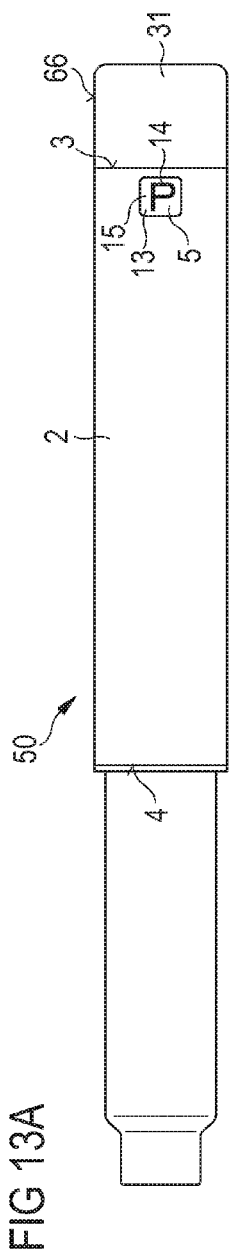
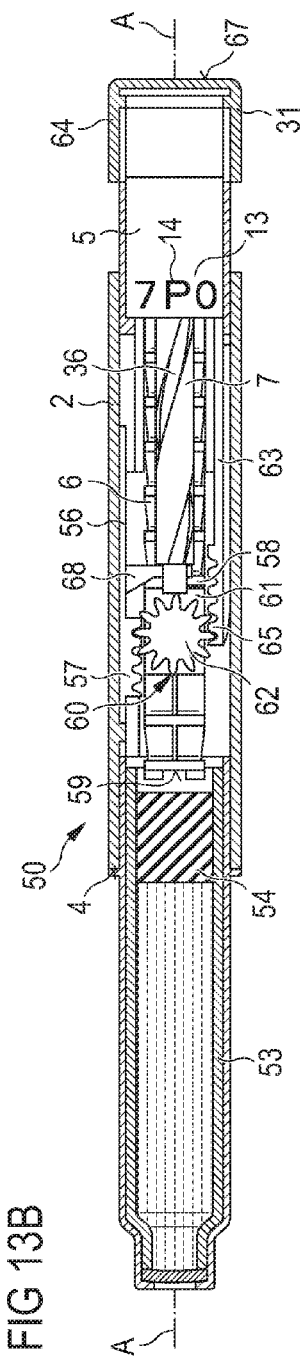
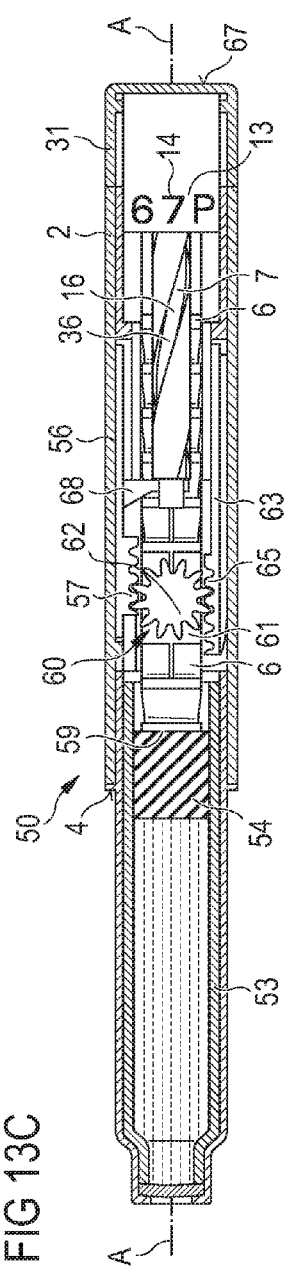
FIG 13A
FIG 13B
FIG 13C

DRIVE ASSEMBLY SUITABLE FOR USE IN A DRUG DELIVERY DEVICE AND DRUG DELIVERY DEVICE

CROSS REFERENCE TO RELATED APPLICATIONS

The present application claims priority to International Application No. PCT/EP2009/003310 filed on May 9, 2009, which claims the priority of European patent applications EP 08009260.4, filed on May 20, 2008, and EP 08011676.7 filed on Jun. 27, 2008. The entire disclosure content of these applications is herewith incorporated by reference into the present application.

TECHNICAL FIELD

The present invention relates to a drive assembly suitable for use in a drug delivery device, preferably a pen-type injector, by which a number of pre-set doses of a medicinal product can be administered. In particular, the present invention relates to such a drug delivery device where a user may activate the drug delivery device.

PRIOR ART

Such drug delivery devices have application where persons without formal medical training, i.e., patients, need to administer an accurate and predefined dose of a medicinal product, such as heparin or insulin. In particular, such devices have application where medicinal product is administered on a regular basis over a short-term or long-term period.

These circumstances set a number of requirements drug delivery devices of this kind should meet. The device should be robust in construction, yet easy to use in terms of the manipulation of the parts, understanding by a user of its operation and the delivery of the required dose of medicament. Dose setting should be easy and unambiguous. Where the device is to be disposable rather than reusable, the device should be cheap to manufacture and easy to dispose of (preferably being suitable for recycling). To meet these requirements the number of parts required to assemble the device and the number of material types the device is made from should be kept to a minimum.

In particular a drive assembly for a drug delivery device should be provided which facilitates making available information about the number of doses of a drug already dispensed from a drug delivery device or the number of doses of a drug remaining for dispense in a drug delivery device.

In EP 1690561 A2 a syringe is taught that has a plunger which is pulled away from a rear end of a syringe housing to set a dose. During pulling back of the plunger a sleeve is indexed round with the sleeve having letters on the outside corresponding to days of the week. When the plunger is moved forward, the sleeve remains static. Thus, this device is not intended for providing information about a number of doses.

DISCLOSURE OF THE INVENTION

According to at least one aspect a drive assembly is provided for. The drive assembly may be a drive assembly for use in a drug delivery device.

According to at least one aspect the drive assembly comprises a housing. The housing preferably has a proximal end and a distal end. An axis may extend between the proximal end and the distal end.

According to at least one aspect the drive assembly comprises at least one drive member. The drive member may be a drive sleeve, for example. The drive member may be arranged on the side of the proximal end. The drive member preferably transmits mechanical energy for operating the drive assembly. By means of the drive member kinetic energy may be transmitted for operating the drive assembly. The drive member may be configured to be moveable along the axis. Preferably, the drive member is configured to be moveable only along the axis. In other words, the drive member is preferably non-rotable around the axis. Kinetic energy may be transmitted by means of the drive member, for example by moving the drive member with respect to the housing. A drug delivery device incorporating a drive assembly may be driven by a push/pull mechanism or any other mechanism known by those skilled in the art. Rotation of the drive member, e.g. for setting a dose, is not required.

According to at least one aspect the drive assembly comprises a piston rod. The piston rod is preferably adapted to be driven along the axis, in particular distally away from the proximal end. The piston rod may be driveable along the axis by means of the drive member and in particular by kinetic energy provided by the drive member. The piston rod may be moved along the axis with respect to the housing, in particular distally away from the proximal end. Piston rod may drive delivery of a drug from a drug cartridge.

According to at least one aspect the drive assembly comprises an indicator. The indicator may be adapted to provide information linked to or about a position of the piston rod relative to the proximal end and/or the distal end of the housing. Preferably, the position is a position of the piston rod within the housing. The indicator may be adapted to provide unambiguous information about the position of the piston rod. Preferably, the indicator is adapted to provide different information for different positions of the piston rod. In particular, the indicator may be adapted to provide information linked to a distance of the piston rod from the proximal end and/or the distal end. The indicator may be configured to provide information linked to a plurality of different distances of the piston rod from the proximal end, with the information which is provided preferably being different for two different distances. The indicator is preferably configured to be rotatable around the axis. Indicator and piston rod may be arranged on the axis.

According to at least one aspect the indicator and the piston rod are configured to convert a relative movement of indicator and piston rod with respect to one another into a rotational movement of the indicator. Piston rod and indicator may be coupled to one another, either directly or indirectly, for converting their relative movement into rotational movement of the indicator.

The relative movement of piston rod and indicator which is converted into rotational movement of the indicator may be or may comprise relative movement along the axis and/or relative rotational movement.

Relative movement of the indicator and the piston rod with respect to one another may comprise movement of the indicator or of the piston rod with respect to the housing.

Rotational movement of the indicator may be or may comprise rotational movement with respect to the housing and/or with respect to the piston rod.

According to at least one aspect the indicator and the piston rod are configured to convert a movement of the piston rod with respect to the housing into a rotational movement of the indicator. In this case, indicator and piston rod do not have to move relative to one another in the axial direction for achieving rotational movement of the indicator. Piston rod and indicator may be coupled to one another, either directly or indirectly, for converting movement of the piston rod with respect to the housing into rotational movement of the indicator.

The rotational movement of the indicator is preferably a rotational movement around the axis. Thus, the rotation angle of the indicator may be indicative of the position of the piston rod relative to the proximal end and/or the distal end. The rotation angle of the indicator may be directly linked to the distance of the piston rod from the proximal end and/or the distal end.

The movement of the piston rod with respect to the housing which is converted into rotational movement of the indicator may be or may comprise movement of the piston rod along the axis with respect to the housing and/or rotational movement of the piston rod with respect to the housing.

Rotational movement of the indicator may be or may comprise rotational movement with respect to the housing and/or with respect to the piston rod.

According to at least one aspect the drive assembly is configured to move the piston rod unidirectionally along the axis. Preferably, the drive assembly is configured to move the piston rod unidirectionally with respect to the housing, in particular away from the proximal end in the distal direction, preferably only away from the proximal end. Of course, when the drive assembly is reset in an initial condition, for example after all doses of a drug have been dispensed from a cartridge and the cartridge is substituted by a new one, movement in the proximal direction of the piston rod may be allowed.

According to at least one aspect the drive assembly is configured to move the indicator in unidirectional rotational movement. The unidirectional rotational movement may either be clockwise or counter-clockwise. Of course, when the drive assembly is reset in an initial condition rotational movement of the indicator in the other direction may be allowed.

According to at least one aspect the drive assembly comprises a rotation member. The indicator may comprise the rotation member. The rotation member is preferably configured to convert relative movement of indicator and piston rod with respect to one another and/or movement of the piston rod with respect to the housing into rotational movement of the indicator. The indicator may be coupleable or permanently coupled to the piston rod via the rotation member. This coupling may be a direct or indirect coupling. Rotation of the rotation member expediently results in rotational movement of the indicator. Indicator or an indicator part thereof and rotation member may be unitary or discrete components. Of course, with respect to the number of parts of the drive assembly being as low as possible the unitary configuration of indicator and rotation member is preferred.

According to at least one aspect at least a part of the rotation member is arranged between the piston rod and the axis. At least a part of the rotation member or the rotation member and, preferably, the indicator may be arranged within the piston rod. This arrangement of the rotation member allows for facilitated implementation of the indicator in a drive assembly that has driving elements that are arranged on the outside of the piston rod, like elements that mechanically contact the housing, for example by engaging the housing. Additionally, an arrangement of the rotation member nearer to the axis than the piston rod facilitates a compact design of the drive assembly. Furthermore, the degrees of freedom on where to arrange the indicator in the drive assembly are increased, because the part of the rotation member may be arranged between the piston rod and the axis. Preferably, that part of the rotation member which is arranged within the piston rod is also provided to interact with the piston rod for converting movement of the piston rod with respect to the housing into rotational movement of the indicator. Consequently, coupling between rotation member and piston rod can be achieved via the rotation member from within the piston rod, for example by engagement and/or mechanical interaction of piston rod and indicator. An external feature on the outside of the rotation member, e.g. on an outer wall, may be arranged to mechanically interact with an internal feature provided within, e.g. on an inner wall of, the piston rod. If the rotation member or the indicator was arranged completely outside of the piston rod, for example as an indicator sleeve surrounding the piston rod, it would be necessary for the indicator to be arranged near the distal end of the housing in such a way that the piston rod which travels through the indicator can still couple to the indicator even if the piston rod has already moved a considerable distance in the distal direction. This can be avoided on account of the rotation member, because the rotation member can be configured to couple piston rod and indicator, whereas a different indicator part of the indicator can be used for providing (displaying) information.

According to at least one aspect the indicator has an indication surface, e.g. one or more than one indication surface. The indication surface is preferably provided with a plurality of index elements. The index elements preferably are discrete index elements. The index elements may be adapted to provide discrete information about the number of doses remaining in a drug delivery device and/or about the number of doses dispensed from the device, when the drive assembly is implemented in a drug delivery device. Index elements may comprise digits, numbers and/or letters. The letter P may be used to indicate, that the prime dose is still available in the device, for example. The letter D may be used to indicate that the prime dose has been already dispensed, for example. Digits and/or numbers may indicate the number of doses taken and/or remaining in the device.

The indication surface is preferably configured to be rotatable with respect to the housing and/or the piston rod. Rotation of the indication surface may be achieved by the relative movement of the piston rod and the indicator with respect to one another and/or by the movement of the piston rod with respect to the housing that is converted into rotational movement of the indicator. The indication surface may be rotatable around the axis.

The indicator may comprise an indication position. If an index element is located in indication position, the user knows that this particular index element provides for the relevant information linked to the current position of the piston rod. When the indicator is rotated, a first index element in indication position may be replaced by a second index element in indication position.

It is preferred for the drive assembly to be configured for at least one of the index elements being visible from outside of the drive assembly. Expediently, at least the index element which is in indication position is visible from the outside. Index elements not in indication position may be invisible from the outside. The housing or the drive member may comprise a window, for example a recess or a transparent portion, for rendering an index element visible from the outside, preferably only when the index element is in indication position.

During rotation of the indication surface, different index elements may become visible from the outside through the window. The position of the window may define the indication position of the indicator, for example.

According to at least one aspect the indicator is moveable along the axis. The indicator may be movable with respect to the housing and/or with respect to the piston rod.

According to at least one aspect the drive member is moveable along the axis with respect to the housing. The indicator may be coupled to the drive member with the indicator following an axial movement of the drive member.

According to at least one aspect the drive assembly is configured to convert movement of the indicator along the axis away from or towards the distal end of the housing into rotational movement of the indicator. Preferably, the drive member is moveable along the axis and the indicator is coupled to the drive member with the indicator following an axial movement of the drive member, e.g. proximal and/or distal movement of the drive member, like movement of the drive member away from or towards the distal end of the housing. It is particularly preferred that movement of the indicator towards the distal end is converted into rotational movement of the indicator. During movement of the indicator away from the distal end rotation of the indicator may be restricted or prevented. If a dose to be delivered is set by moving the drive member away from the distal end with the indicator following that movement, rotational movement of the indicator can be prevented during setting. Thus, rotation of the indicator only takes place, when the indicator is moved towards the distal end, i.e. during dose dispense. Consequently, the index element in indication position is linked to the position of the piston rod relative to the proximal end even if the dose is set and has not yet been dispensed. During dose dispense, the indicator may rotate.

According to at least one aspect the drive assembly is configured to convert a distal movement of the piston rod along the axis away from the proximal end (in the distal direction) into rotational movement of the indicator.

According to at least one aspect the drive assembly is configured to restrict or prevent distal movement of the indicator along the axis towards the distal end with respect to the housing and/or with respect to the drive member. For example, movement towards the distal end may be restricted or prevented by a mechanical stop of the drive assembly. The indicator, for example an indicator part thereof that comprises the indication surface, may mechanically contact the mechanical stop. The drive member or the housing may comprise the mechanical stop.

According to at least one aspect the drive assembly is configured to restrict or prevent rotational movement of the piston rod with respect to the housing. Preferably, the drive assembly is configured to move the piston rod along the axis only. Rotational movement of the piston rod with respect to the housing may thus be avoided. Manufacturing of the drive assembly can be facilitated. Even though the indicator can rotate around the axis with respect to the housing due to a coupling between indicator and piston rod, the piston rod is preferably coupled to the housing such that rotation of the piston rod with respect to the housing is avoided. The piston rod can be coupled to the housing by a splined coupling, for example.

According to at least one aspect the drive assembly is configured to move the piston rod, preferably distally, along the axis and to rotate the piston rod. In particular, the drive assembly may be configured to move the piston rod along the axis and to rotate the piston rod simultaneously. The axis is preferably the rotation axis of the rotational movement of the piston rod. Thus the piston rod can move with respect to the housing translational along the axis and rotational around the axis. When a dose of a drug is to be delivered from a drug delivery device, this may be caused by distal movement of the piston rod along the axis. The piston rod may mechanically interact with a piston of a drug cartridge of a drug delivery device.

According to at least one aspect the indicator is coupleable or permanently coupled to the piston rod with the coupling being configured to convert rotational movement of the piston rod into rotational movement of the indicator. Preferably, a rotational movement of the piston rod is converted into rotational movement of the indicator of equal rotation angles. That is to say, if the piston rod is rotated by an angle, the indicator is rotated by the same angle. The indicator follows the rotational movement of the piston rod. The piston rod of course additionally moves along the axis in the distal direction.

According to at least one aspect the indicator is coupleable or coupled to the piston rod by a spline. For example, the rotation member and the piston rod may be configured to be coupleable or coupled by a splined connection. The rotation member may be a splined shaft, for example. Rotational movement of indicator and piston rod of the same rotation angle is facilitated therewith.

According to at least one aspect the indicator is coupleable or permanently coupled to the piston rod with the coupling being configured to convert rotational movement of the piston rod into rotational movement of the indicator of different rotation angles. That is to say, if the piston rod rotates by a first angle, the indicator rotates by a second angle which is different from the first one. It is preferred that the indicator rotates less, i.e. by a smaller angle, than the piston rod. The number of index elements provided on the indication surface can be increased in this way.

According to at least one aspect the indicator is coupleable or permanently coupled to the piston rod with the coupling being configured for rotational movement of piston rod and indicator with respect to one another.

According to at least one aspect the drive assembly is configured for the piston rod and the indicator to rotate in the same direction or in different directions.

According to at least one aspect the indicator is coupleable or permanently coupled to the piston rod with the coupling being configured to prevent rotational movement of the piston rod relative to the indicator, preferably being configured for pure translational movement of the piston rod relative to the indicator.

According to at least one aspect the drive assembly is configured for the indicator being decoupleable from the piston rod. Thus, the piston rod may be moved along the axis with respect to the housing and/or with respect to the piston rod in a region without movement of the piston rod with respect to the housing and/or relative movement of indicator and piston rod being converted into rotational movement of the indicator in this region. The rotation member may be arranged between the piston rod and the axis and/or within the piston rod in this region. In another region, the movement of the piston rod is converted into rotational movement of the indicator. The rotation member may be arranged between the piston rod and the axis, e.g. within the piston rod, in this region, too.

According to at least one aspect at least one of the rotation member and the piston rod has a protrusion. Both of the rotation member and the piston rod may have a respective protrusion. Preferably, the protrusion is configured to mechanically interact, e.g. by mechanical contact or engagement, with the other one of the rotation member and the piston rod for converting relative movement of the piston rod and the rotation member and/or for converting movement of the piston rod with respect to the housing into rotational movement of the rotation member with respect to the housing. Rotational movement of the rotation member of course results in rotational movement of the indicator.

The protrusion may comprise one of a male thread, a rib, a knob, a pin or a lug. The male thread may be a helical thread. The helical thread preferably extends along the axis.

The protrusion of the rotation member may be configured to mechanically interact with the protrusion of the piston rod, e.g. by mechanical contact or engagement of the protrusions.

According to at least one aspect at least one of the rotation member and the piston rod has an indentation. Preferably, the indentation is configured to mechanically interact, e.g. by mechanical contact or engagement, with the other one of the rotation member and the piston rod for converting relative movement of the piston rod and the rotation member and/or for converting movement of the piston rod with respect to the housing into rotational movement of the rotation member. Rotational movement of the rotation member of course results in rotational movement of the indicator.

The indentation may comprise one of a slit and a female thread. The thread may be a helical thread. The helical thread may extend along the axis.

According to at least one aspect the protrusion of the rotation member or of the piston rod engages the indentation of the other one of the rotation member and the piston rod.

According to at least one aspect the rotation member has a section that is configured to threadedly engage the piston rod.

According to at least one aspect the piston rod engages the housing. The piston rod may threadedly engage the housing. Rotational movement of the piston rod around the axis and/or translational movement of the piston rod along the axis may be facilitated therewith.

A pitch of a thread for a threaded engagement of the rotation member and the piston rod may be different from the pitch of a thread for a threaded engagement of the piston rod and the housing. Different rotation angles of the rotation of the piston rod with respect to the housing and of the rotation of the indicator with respect to the housing may thus be achieved.

According to at least one aspect the indicator engages the housing or the drive member. The indicator may threadedly engage the housing or the drive member.

According to at least one aspect the indicator comprises a plurality of indication surfaces which are arranged side by side along the axis. The number of index elements of the indicator of a given size and arranged at a given distance with respect to one another can be increased in this way.

Two indication surfaces may be coupled to one another by an odometer-like mechanism. For example, a 360° rotation of one of the indication surfaces may result in a rotation of the other indication surface by a smaller rotation angle.

The drive assembly may be configured to replace a first index element of one indication surface which is in indication position with a second index element of another indication surface in indication position by rotating the indication surfaces. A threaded engagement of the indicator with the housing or with the drive member is particularly expedient for this purpose. The indication surfaces may be part of a thread.

For example, during rotation of the indicator a first indication surface which was visible from the outside through a window may be replaced by a second indication surface which is rotated (and translated) under the window.

According to at least one aspect, a drive assembly for use in a drug delivery device comprises:
  a housing having a proximal and distal end;
  a non-rotatable drive member;
  a piston rod engaged with the said drive member, preferably by an engagement means;
wherein,
  a) when the said drive member moves proximally with respect to the said housing the said piston rod does not move with respect to the said housing;
  b) when the said drive member moves distally the said piston rod rotates with respect to the said housing so that a force is transferred in the longitudinal direction towards the distal end of the said drug delivery device.

According to at least one aspect, a drive assembly for use in a drug delivery device is provided, comprising:
  a housing having a proximal and a distal end;
  a drive member located within the said housing such that the said drive member is movable longitudinally;
  a piston rod adapted to operate through the housing and transfer a force in the longitudinal direction towards the distal end of the drug delivery device;
  a rotating means releasably engaged with the said piston rod and engaged to the said drive member and engaged to the said housing;
characterized in that,
  a) when the said drive member moves proximally with respect to the said housing the said rotating means moves proximally with respect to the said piston rod;
  b) when the said drive member moves distally the said rotating means moves distally displacing the said piston rod towards the distal end of the device.

The aspects described above may be combined with one another and may also be combined with features and aspects described further below.

According to a particularly preferred embodiment, a drive assembly for use in a drug delivery device comprises:
  a housing having a proximal end and a distal end;
  an axis extending between the proximal end and the distal end;
  at least one drive member;
  a piston rod adapted to be driven along the axis by the drive member;
  an indicator adapted to provide positional information about a position of the piston rod relative to the proximal end,
  wherein
  the indicator and the piston rod are configured to convert a movement of the piston rod with respect to the housing into a rotational movement of the indicator with respect to the housing.

Thus, via the rotation angle of the rotation of the indicator with respect to the housing, positional information about the position of the piston rod relative to the proximal end can be gathered. In particular, the rotation angle can be directly linked to the position of the piston rod relative to the proximal end and in particular to the position of the piston rod within the housing. Thus, reliable information about the number of doses remaining in or dispensed from a drug delivery device, preferably from a drug cartridge of the drug delivery device comprising the drive assembly can be provided to a user.

According to at least one aspect a drug delivery device is provided for, the drug delivery device comprising the drive assembly as described above. The drug delivery device can comprise a plurality of doses of a drug. The doses may be provided for in a drug cartridge of the device.

The indicator can be adapted to provide a discrete indication concerning the number of doses available in the device or concerning the number of doses already dispensed from the device.

The drug delivery device may be a pen-type device. The drug delivery device may be an injector-type device. The drug delivery device may comprise a needle or may be a needle-free device.

The drug delivery device is preferably adapted to provide fixed doses of the drug, i.e. a pre-given amount of the drug in every delivery process.

The piston rod may be configured to drive delivery of the drug from the drug cartridge when the piston rod is moved distally along the axis.

The drive assembly described herein above and below may be configured for the indicator being actuated, i.e. rotated, when a dose is dispensed, for example by moving the drive member towards the distal end, from the drug delivery device, preferably only during dose dispense. Thus, when a dose is set, for example by moving the drive member away from the distal end, rotational movement of the indicator may be restricted or prevented. Accordingly, the indicator may still have the index element in indication position which is indicative of the current position of the piston rod after the dose has been set, i.e. the correct index element is in indication position. If the indicator was rotated during dose setting, an index element that is indicative of the position of the piston rod after the dose which was set has been dispensed might be put into indication position, i.e. an incorrect index element might be in indication position. Incorrect index elements in indication position can be avoided by preventing or restricting rotational movement of the indicator during dose setting, for example by a detent element.

At least one other aspect relates to the use of a drug delivery device as described above for dispensing a medicinal product, preferably for dispensing a pharmaceutical formulation (e.g. solution, suspension etc.). The medicinal product or the pharmaceutical formulation may comprise an active compound selected from the group consisting of insulin, growth hormone, low molecular weight heparin, their analogues and their derivatives.

The term "drug delivery device" shall preferably mean a single-dose or multi-dose or pre-set dose or pre-defined, disposable or re-useable device designed to dispense a user selectable or pre-defined dose of a medicinal product, preferably multiple pre-defined doses, e.g. insulin, growth hormones, low molecular weight heparins, and their analogues and/or derivatives etc. Said device may be of any shape, e.g. compact or pen-type. Dose delivery may be provided through a mechanical (optionally manual) or electrical drive assembly or stored energy drive assembly, such as a spring, etc. Dose setting may be provided through a manual mechanism or electronic mechanism. Additionally, said device may contain components designed to monitor physiological properties such as blood glucose levels, etc. Furthermore, the device may comprise a needle or may be needle-free. In particular, the term "drug delivery device" preferably means a disposable needle-based pen-type device providing multiple pre-defined doses having mechanical and manual dose delivery and dose setting mechanisms, which is designed for use by persons without formal medical training such as patients. Preferably, the drug delivery device is of the injector-type.

The term "housing" shall preferably mean any exterior housing ("main housing", "body", "shell") or interior housing ("insert", "inner body"), e.g. having a unidirectional axial coupling to prevent proximal movement of specific components. The housing may be designed to enable the safe, correct, and comfortable handling of the drug delivery device or any of its mechanism(s). Usually, it is designed to house, fix, protect, guide, and/or engage with any of the inner components of the drug delivery device (e.g., the drive assembly, cartridge, plunger, piston rod) by limiting the exposure to contaminants, such as liquid, dust, dirt etc. In general, the housing may be unitary or a multipart component of tubular or non-tubular shape. Usually, the exterior housing serves to house a cartridge from which a number of doses of a medicinal product may by dispensed. Preferably, the exterior housing is provided with a plurality of maximum dose stops adapted to be abutted by an axial stop provided on the drive member. The piston rod may be coupleable or coupled to the housing.

The term "drive assembly" shall preferably mean a part of a drug delivery device to which a drug cartridge is coupleable or (permanently) coupled. The drive assembly may thus include indicator, housing and/or piston rod. Furthermore, additional elements may be present in the drive assembly, like a mechanical support, for example or other elements described above or below. The elements of the drive assembly may be formed as described above and below.

The term "engaged" shall preferably mean the interlocking of two or more components of the drive assembly/drug delivery device, e.g. a spline, thread, or meshed teeth connection, preferably the interlocking of meshed teeth of components.

The term "drive member" shall preferably mean any component adapted to operate through/within the housing, designed to translate axial movement through/within the drug delivery device, e.g. from an actuation means to the piston rod. In a preferred embodiment the drive member is further releasably engaged with the piston rod. The drive member may be of unitary or multipart construction.

The term "piston rod" shall preferably mean a component adapted to operate through/within the housing, designed to transfer axial movement through/within the drug delivery device, preferably from the drive member to the piston of a cartridge, e.g. for the purpose of discharging/dispensing an injectable product from the cartridge. Said piston rod may be flexible or not. It may be a simple rod, a lead-screw, a rack and pinion system, a worm gear system, or the like. The term "piston rod" shall further preferably mean a component having a circular or non-circular cross-section. It may be made of any suitable material known by a person skilled in the art and may be of unitary or multipart construction. The piston rod may comprise a series of one or more sets of longitudinally spaced ribs and/or indentations. The piston rod may comprise a male or a female thread. A male or female thread may be arranged on the outside of the piston rod and/or within the piston rod.

The term "rotating means" shall preferably mean any rotating component that transfers force and/or movement from the drive member to the piston rod. It may be made of any suitable material known by a person skilled in the art and may be of unitary or multipart construction. In a preferred embodiment the rotating means may be a gear component, more preferably a spur gear.

The term "gear" shall preferably mean a toothed wheel used in conjunction with a rack and/or another gear, preferably a rack, to transmit force and/or motion. In a preferred embodiment the gear may be a spur gear. In yet another preferred embodiment the term "gear" means a gear wheel mounted within a carrier.

The term "rack" shall preferably mean any component having a linear array of ribs and/or indentations and/or gear-form teeth. In a preferred embodiment a rack is located in the housing and a further rack is located in the drive member. In a further preferred embodiment one and/or both, more preferably one, of the racks located on the housing or on the drive member is flexible and/or pivoted and/or movable in one or more axis, more preferably one.

The "distal end" of the device or a component of the device, e.g. of the housing, shall preferably mean the end, which is to be disposed closest or which is disposed closest to the dispensing end of the device.

The "proximal end" of the device or a component of the device, e.g. the housing, shall mean the end, which is to be disposed furthest away or which is furthest away from the dispensing end of the device.

The term "helical thread" shall preferably mean a full or part thread, e.g., a cylindrical spiral rib/groove, located on the internal and/or external surface of a component of the drug delivery device, like piston rod, housing, drive member or indicator, for example. The thread preferably has an essentially triangular or square or rounded section. The section may be designed to allow continuous free rotation and/or axial movement between components. Optionally, a thread may be further designed to prevent rotational and/or axial movement of certain components in one direction, e.g. in axial direction and/or in rotational direction around the axis.

BRIEF DESCRIPTION OF THE DRAWINGS

Without any limitation, e.g. to the scope of the claims, preferred embodiments are described below with reference to the drawings in which:

FIG. 7 shows an oblique sectional view of a seventh embodiment of the drive assembly.

FIG. 8 shows an oblique sectional view of an eighth embodiment of the drive assembly.

FIG. 12 schematically illustrates the relative movement of piston rod and indicator with respect to one another for a situation similar to the tenth embodiment.

FIG. 13A shows a side view of the first embodiment of the drug delivery device in a first, e.g. cartridge full, position.

FIG. 13B shows a sectional view of the first embodiment of the drug delivery device in a second, e.g. first dose set, position.

FIG. 13C shows a sectional view of the first embodiment of the drug delivery device in a third, e.g. first dose dispensed, position.

Like elements, elements of the same kind and identically acting elements are provided with the same reference numerals in the figures.

DETAILED DESCRIPTION

Figure 1:
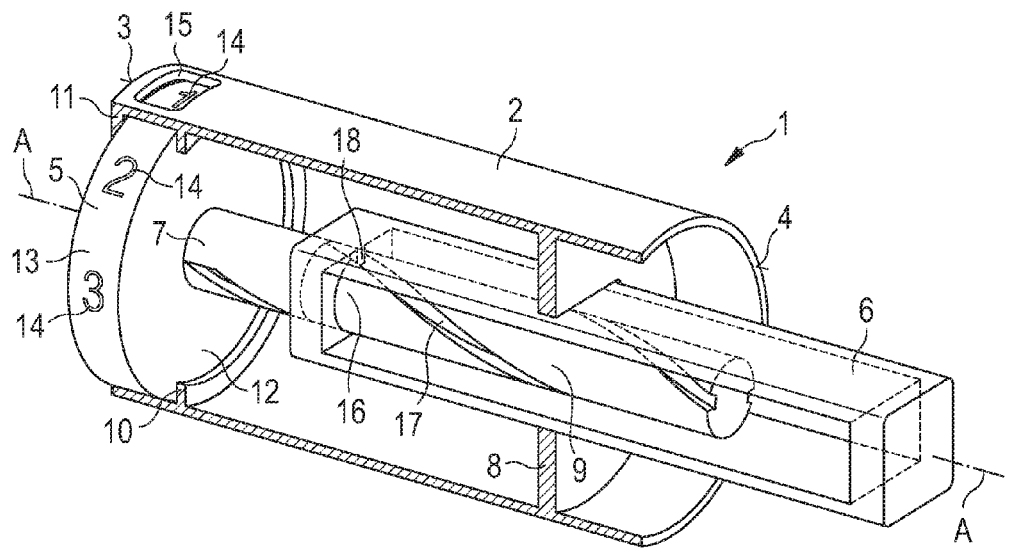
FIG. 1 shows an oblique sectional view of a first embodiment of a drive assembly.
Figure 1A:
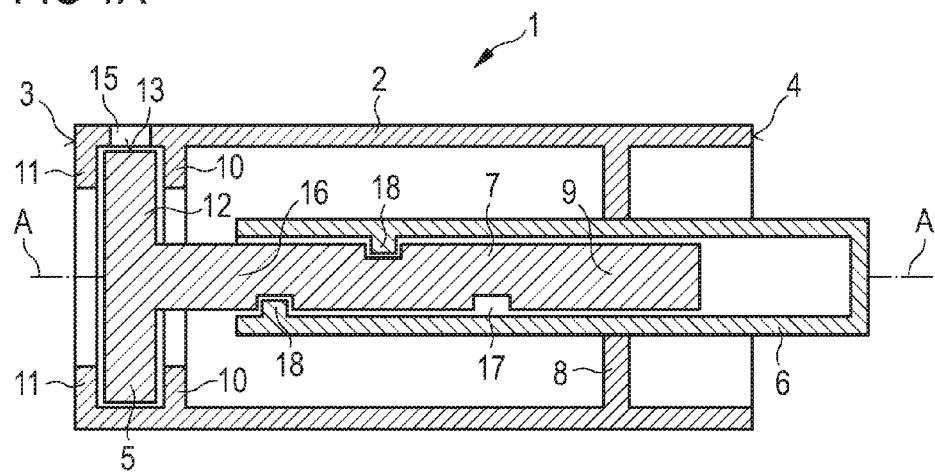
FIG. 1A shows a sectional view of the first embodiment of the drive assembly.

FIG. 1 shows an oblique sectional view of a first embodiment of a drive assembly. FIG. 1A shows a sectional view of the first embodiment of the drive assembly.

The drive assembly 1 according to FIGS. 1 and 1A comprises a housing 2. The housing has a proximal end 3 and a distal end 4. An axis A extends between the proximal end 3 and the distal end 4. The drive assembly 1 comprises an indicator 5. Additionally, the drive assembly 1 has a piston rod 6. Indicator 5 and piston rod 6 are located within the housing 2. Furthermore, indicator 5 and piston rod 6 are arranged on the axis. Thus, axis A can run through piston rod 6 and indicator 5. The housing 2 may have a tubular shape. The rotation member 7 can be formed shaft-like.

The drive assembly 1 comprises a rotation member 7. Rotation member 7 is arranged within the housing 2. A main (longitudinal) direction of extent of piston rod 6 and/or rotation member 7 is aligned along the axis A. Rotation member 7 and indicator 5 can be formed as separate elements or unitary, i.e. rotation member 7 can be part of the indicator 5. Indicator 5, piston rod 6 and/or rotation member 7 can be retained in housing 2. Piston rod 6 is moveable along axis A in the distal direction with respect to the housing 2. Indicator 5 is rotatable around axis A with respect to the housing 2. Axial movement of the indicator 5 is restricted. Preferably, axial movement in the distal direction and/or in the proximal direction is restricted.

A partial region of the rotation member 7 extends axially into piston rod 6. The rotation member 7 is arranged between piston rod 6 and axis A in that region. The rotation member 7 can extend from outside of the piston rod into the piston rod 6.

Indicator 5, piston rod 6 and/or rotation member 7 can be secured against displacement with respect to the axis A in radial direction. The drive assembly 1 comprises a mechanical support 8. The mechanical support may be configured to secure indicator 5, piston rod 6 and/or rotation member 7 against displacement in the radial direction.

The mechanical support 8 is preferably configured to provide mechanical support for piston rod 6. The mechanical support 8 may also provide mechanical support to rotation member 7. Alternatively, a separate mechanical support can be provided for supporting rotation member 7 (not explicitly shown). Piston rod 6 can be in mechanical contact with mechanical support 8. Mechanical support 8 can be formed unitary with the housing 2 or as a separate element that is connected to the housing, in particular to an inner wall thereof. The mechanical support 8 can protrude from an inner wall of housing 2.

The piston rod 6 can extend through the mechanical support 8, for example through an opening 9 thereof, e.g. a cut-out or a hole.

The piston rod 6 is preferably coupled to the housing 2 for non-rotational movement of the piston rod with respect to the housing. The piston rod can be coupled to the housing by means of a splined connection, for example. A coupling that prevents rotational movement of the piston rod 6 relative to the housing 2 may be achieved via mechanical support 8. The opening 9 in mechanical support 8 can be formed chiseled for the purpose of non-rotational coupling of the piston rod 6 to the housing 2. The opening can have a rectangular or square cross section for this purpose, for example.

The cross section of the opening 9 and the cross section of the piston rod 6 may correspond to one another when view along the axis A. The piston rod can for example have a rectangular or square cross section. Rotation of the piston rod is thus prevented by opening 9 which restrains or prevents a rotational movement of the piston rod 6.

The piston rod 6 is arranged moveable along the axis A and in particular within housing 2. Preferably, the piston rod 6 is arranged for pure translational movement along the axis. Furthermore, the drive assembly 1 is preferably configured to move the piston rod unidirectional along the axis in the distal direction away from the proximal end 3 of housing 2.

The indicator 5 is secured against axial movement of the indicator relative to housing 2 and/or piston rod 6. Thus, the piston rod 6 may be moved in the distal direction with respect to indicator 5 and housing 2, the indicator may not be moved axially with respect to the housing.

The drive assembly 1 comprises a mechanical stop 10. Mechanical stop 10 can protrude from an inner wall of the housing. Mechanical stop 10 is preferably configured to prevent movement of the indicator away from proximal end 3 and/or towards distal end 4. Preferably, drive assembly 1 comprises an additional mechanical stop 11. Mechanical stop 11 can be embodied according to mechanical stop 10. Mechanical stop 11 is preferably configured to prevent proximal movement of the indicator away from the distal end 4. Mechanical stop 10 and/or 11 can have an annular shape.

Indicator 5 comprises an indication surface 13. Indicator 5 comprises an indicator part 12. Indication surface 13 may be a surface of indicator part 12. Indicator part 12 may be formed disk-like, for example. Mechanical stops 10 and 11 can, for example, cooperate to form a notch that surrounds indicator part 12. Rotation member 7 is preferably connected torque proof to indication surface 13 and/or indicator part 12. The indicator part 12 may protrude radially with respect to the rotation member, which may be shaft-like.

Indication surface 13 is provided with a plurality of index elements 14, preferably discrete indicia. Index elements 14 may comprise digits, i.e. 0 . . . 9, numbers, i.e. greater than 9, and/or one or a plurality of letters.

Index elements 14 can be adapted to provide information linked to the number of doses of a drug remaining in a drug delivery device or dispensed from a drug delivery device, which device comprises the drive assembly and preferably a cartridge containing the drug. Preferably, index elements 14 are adapted to provide information about the number of doses of a drug remaining in a drug delivery device or dispensed from a drug delivery device, which device comprises the drive assembly.

At least one index element 14 which is arranged in indication position is visible from outside of the drive assembly 1. For this purpose, a window 15, for example a transparent portion of the housing 2 or an opening of the housing 2, is provided with the index element in indication position (digit "1" as shown in FIG. 1) being visible through the window from the outside. Index elements not in indication position may be invisible from the outside.

The rotation member 7 can run from outside of the piston rod 6 to inside of the piston rod through an opening 16 of the piston rod, for example a circular opening, like a hole. Opening 16 is preferably provided on that side of the piston rod 6 that faces proximal end 3.

Piston rod 6 and indicator 5 are coupled to one another via rotation member 7 such that movement of the piston rod 6 along the axis, preferably unidirectionally (in the distal direction) away from the proximal end 3, causes rotation of rotation member 7 and thus causes rotation of the indicator 5 and in particular of the indication surface 13. Preferably, the coupling is configured for rotating the indication surface 13 such that an index element 14 rotates into indication position which position was previously occupied by a different index element. Rotation member 7 and piston rod 6 are tightly engaged in this embodiment.

Rotation of the rotation member 7 causes rotation of the indicator 5 and in particular the indication surface 13 thereof. Rotation member is preferably secured against rotation relative to indicator 5.

In order to achieve coupling between rotation member 7 and piston rod 6, rotation member 7 comprises an indentation 17. Indentation 15 may be provided on an outer surface of the rotation member. The indentation 17 can be a thread, for example a helical thread that runs spirally around axis A. The piston rod 6 preferably comprises a protrusion or a plurality of protrusions 18. The respective protrusion 18 can be provided on an inner surface of the piston rod. The respective protrusion 18 can be provided on the side of the piston rod 6 facing the proximal end 3, preferably within opening 16. One protrusion 18 or a plurality of protrusions 18 can be formed as a (single) thread, as part(s) of a thread, as a knob or as a pin. The respective protrusion 18 engages indentation 17, such that piston rod 6 and rotation member 7 engage one another.

On account of a part of the rotation member 7 being arranged within the piston rod and in particular between piston rod 6 and axis A, indicator part 12 and/or indication surface 13 can be positioned freely in the drive assembly. Arranging the indication surface 13 near the distal end 4 is not necessary, because coupling between indicator 5 and piston rod 6 can be achieved via rotation member 7. Arranging the indication surface near the proximal end 3 may improve visibility of the index elements 14 during operation of the drive assembly, for example during dose dispense.

If a drive member (not explicitly shown), which the drive assembly preferably comprises, provides for a force to move piston rod 6 away from the proximal end 3, protrusion 18 engages a side wall of the indentation 17 which is arranged on the side of the indentation facing away from the proximal end 3. By this mechanical contact of protrusion 18 and piston rod 6, rotation member 7 is guided along the thread and caused to rotate. The rotation sense, clockwise or counter-clockwise, is determined by the thread of the rotation member 7. As piston rod 6 travels away from proximal end 3, indicator 5 and in particular indication surface 13 rotates such that the index element 14 visible through the window in FIG. 1 (e.g. digit "1") is replaced by the next index element 14 in line (e.g. digit "2"). Due to the force moving piston rod 6 away from the proximal end 3, indicator part 12 is pressed against mechanical stop 10. Mechanical stop 10 prevents distal movement of the indicator 5. Rotation of the piston rod 6 is prevented by the inner wall of opening 9.

For setting a dose, the drive member may be moved along the axis in the proximal direction, e.g. away from the housing 2. The piston rod 6 does not move during setting. Indicator 5 does not move during setting. For dose delivery (dose dispensing), the drive member may be moved in the distal direction, e.g. towards the housing 2. The movement of the drive member transfers force to the piston rod 6, which moves in the distal direction caused by the force. This distal movement of the piston rod 6, which is coupled to the indicator 5, causes the indicator 5 to rotate. Thus, movement of the piston rod along the axis is converted into rotational movement of the indicator. Piston rod 6 may drive a piston of a drug cartridge (not explicitly shown) in the distal direction resulting in dispensing a dose of a drug from the cartridge.

The rotation angle of indicator 5 and in particular the indication surface 13 thereof, provides information about the distance the piston rod has travelled away from the proximal end. Movement from the piston rod away from the proximal end can cause a dose of a drug to be dispensed from a drug delivery device. The rotation angle can be directly linked to the distance of the piston rod 6 from the proximal end 3. Thus, indicator 5 may provide information that is directly linked to the position of the piston rod relative to the proximal end 3.

Preferably, the drive assembly 1 is configured for the piston rod 6 to be moveable distally away from the proximal end 3 only. Proximal movement of the piston rod 6 may be allowed when a drug delivery device comprising the drive mechanism is reset, for example before replacing or after having replaced a used drug cartridge with another, preferably unused, drug cartridge.

Preferably, the indicator 5 is configured to be rotatable only in one rotation sense, i.e. clockwise or counter-clockwise, when viewed from the same side of the indicator. The indicator may be configured to be rotatable in the other rotation sense only during resetting of the device, for example before replacing or after having replaced a used drug cartridge with another, preferably unused, drug cartridge.

A drive assembly as described above can be easily implemented in a drug delivery device which comprises a piston rod, because only a minor amount of additional or modified elements is necessary.

Of course, alternatively to the situation shown in FIG. 1, the piston rod 6 can comprise an indentation, for example a slit or a female thread, and the rotation member 7 can comprise a protrusion, for example a male thread, for coupling piston rod and rotation member to one another.

The amount by which the indicator 5 rotates, when the piston rod moves a given distance—this distance may correspond to a fixed dose to be dispensed from a drug delivery device—can be adjusted by choosing the pitch of the thread of the rotation member 7 appropriately.

As shown in FIGS. 1 and 1A, if the piston rod moves and is coupled to the rotation member, the indicator rotates in each case. This is due to the helical thread that runs continuously obliquely with respect to the axis A.

Figure 2:
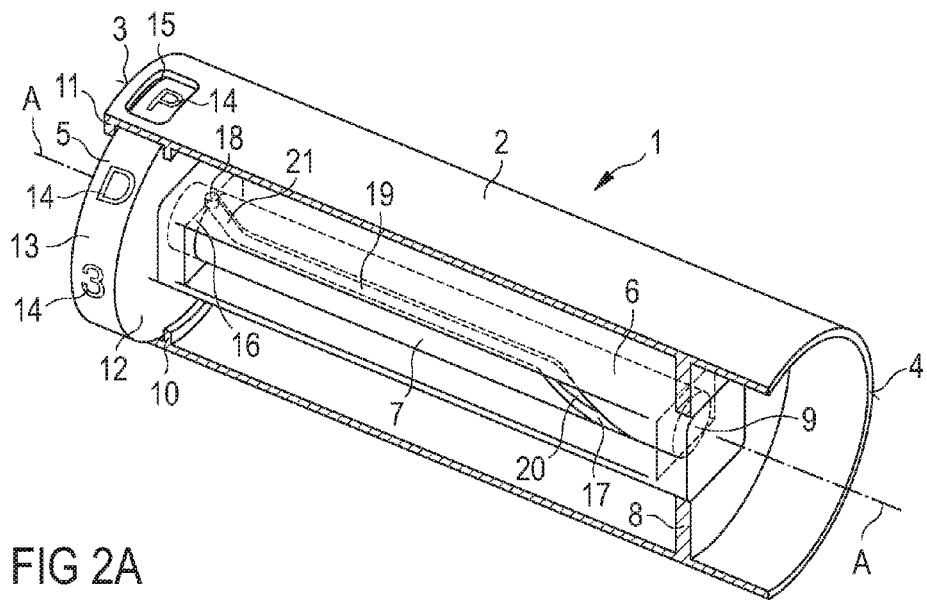
FIG. 2 shows an oblique sectional view of a second embodiment of the drive assembly.
Figure 2A:
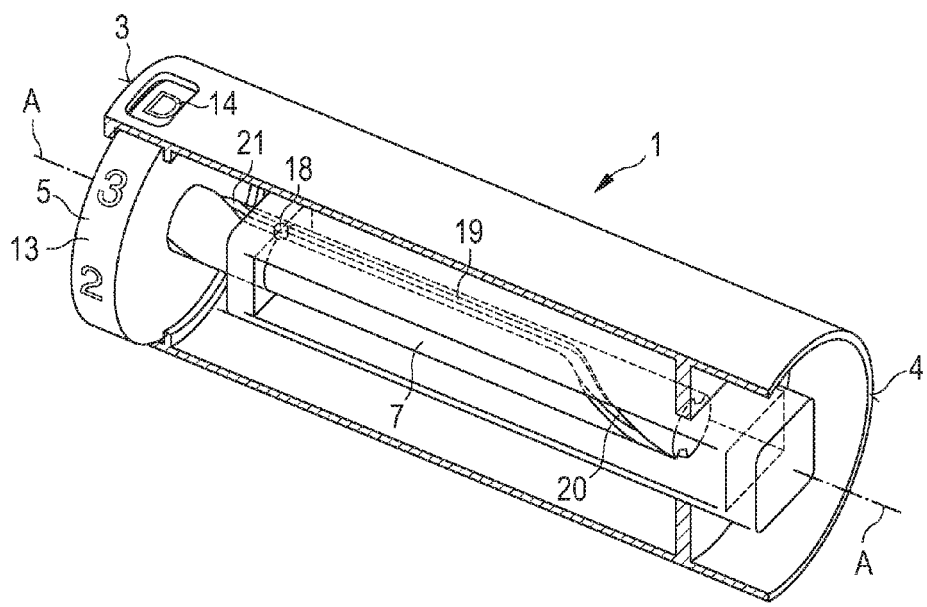
FIG. 2A shows the second embodiment with the piston rod being moved away from the proximal end into a first position.
Figure 2B:
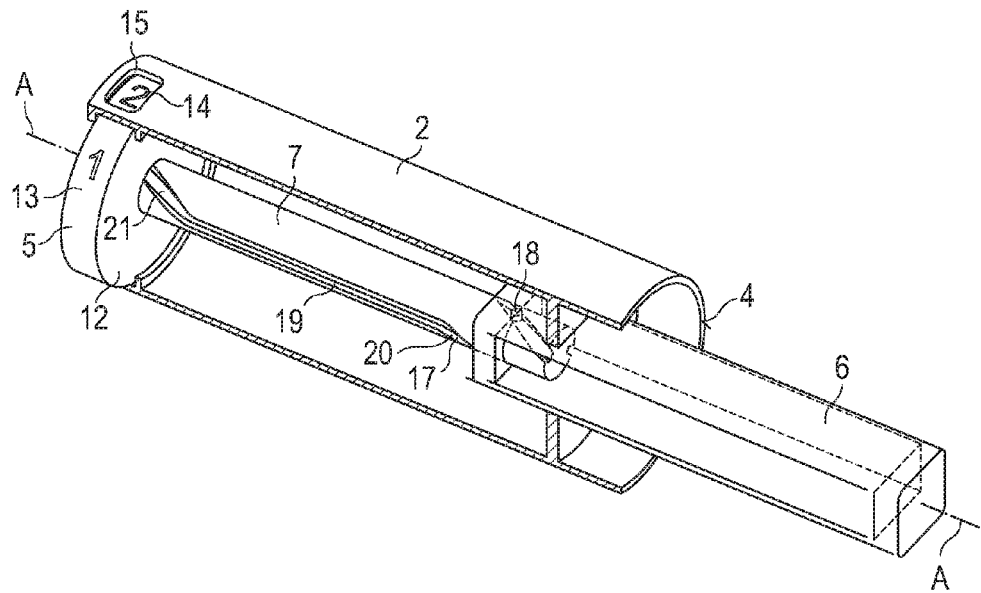
FIG. 2B shows the second embodiment with the piston rod being moved to a second position away from the first position and away from the proximal end.

FIG. 2 shows an oblique sectional view of a second embodiment of the drive assembly 1. FIG. 2A shows the second embodiment with the piston rod being moved distally away from the proximal end into a first position. FIG. 2B shows the second embodiment with the piston rod being moved distally to a second position away from the first position and away from the proximal end. This embodiment essentially corresponds to the embodiment described in connection with FIGS. 1 and 1A.

In contrast to the latter embodiment, indicator 5 and piston rod 6 are coupled to one another with the coupling being configured for rotational movement of the indicator being decoupled from movement along the axis of the piston rod for a given range of movement of the piston rod 6 along the axis A. The rotation member 7 is also arranged within piston rod 6 in that range of movement.

For this purpose, indentation 17 comprises a region 19 that runs parallel to axis A. Therefore, while the protrusion 18 travels within region 19 no rotational movement of the rotation member 7 and thus no rotational movement of indicator 5 is caused. On that side of region 19 that faces distal end 4 a region 20 of indentation 17 can be arranged which runs obliquely with respect to the axis. On that side of the region 19 which faces the proximal end 3, a region 21 of indentation 17 can be arranged in which the indentation 17 runs obliquely with respect to axis A. Region 19 can be arranged between regions 20 and 21. Region 20 and/or region 21 may be a (helical) thread.

Of course, alternatively a protrusion can be used instead of indentation 17 and an indentation instead of protrusion 18.

In regions 20 and 21, in which the indentation 17 runs obliquely with respect to axis A, indicator 5 rotates, when protrusion 18 engages indentation 17 in the respective region and piston rod 6 moves away from proximal end 3. The indicator does not rotate while the protrusion 18 travels along region 19, for example due to additional activations of the drive assembly (e.g. by setting and dispensing additional doses). While protrusion 18 moves along proximal region 21, the indication surface 13 rotates. The index element 14 in indication position changes, for example from letter "P" indicating that the primary dose is still available to letter "D" indicating that a dose has been dispensed from the device. While protrusion 18 moves along distal region 20 the indication surface 13 rotates again. The last few, e.g. three doses, remaining in a drug delivery device can be counted down by rotation of the indicator, which is caused, when protrusion 18 engages distal region 20.

In this embodiment the number of index elements which has to be provided on indication surface 13 can be reduced, because one index element, e.g. "D", may stay in indication position for more than one dose-dispense process. The user still gains information when it is time to obtain a new drug delivery device or a new full drug cartridge which may be operated together with the drive assembly.

As compared to the first embodiment, one region or a plurality of regions of the (helical) thread formed on rotation member 7 can be replaced by a region that runs parallel to axis A, with the indicator not rotating while the rotation member is coupled to the piston rod in the region that runs parallel to axis A.

Figure 3:
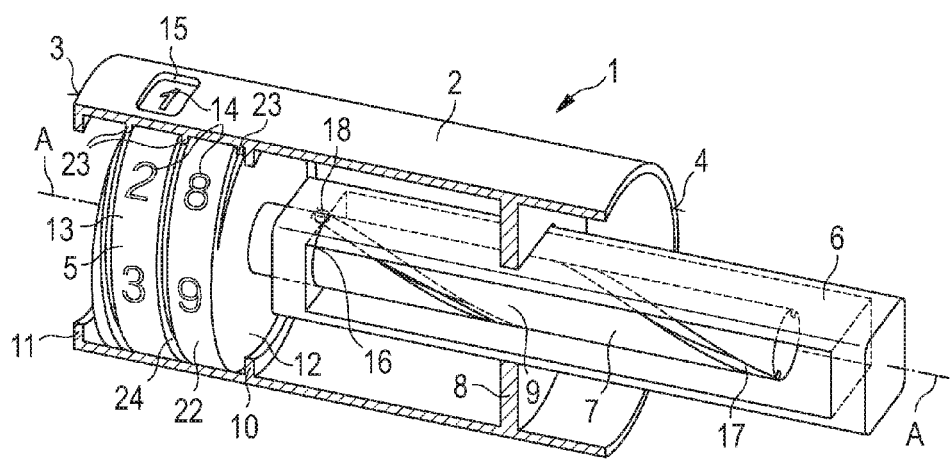
FIG. 3 shows an oblique sectional view of a third embodiment of the drive assembly.

FIG. 3 shows an oblique sectional view of a third embodiment of the drive assembly 1. The third embodiment essentially corresponds to the embodiment described in conjunction with FIGS. 1 and 1A.

In contrast thereto, the drive assembly 1 according to the third embodiment comprises a plurality of indication surfaces, which are arranged side by side along the axis A. For example, indicator 5 comprises two indication surfaces 13 and 22. Each of those indication surfaces can be provided with a plurality of index elements 14. Indication surfaces 13 and 22 may be non-rotatable relative to one another.

In this embodiment, the indicator 5, in particular indicator part 12 thereof, which comprises indication surfaces 13 and 22, is threadedly coupled to the housing 2. Preferably, indicator 5 is threadedly engaged to the housing 2. Housing 2 can comprise a (helical) thread 23 that engages a (helical) thread 24 of indicator part 12.

If the indicator 5 rotates, the indication surface 22 can be rotated into indication position and replace indication surface 13 in this position. That is to say, indication surface 13 can be rotated away from the window and indication surface 22 can be moved under the window, such that one or more index elements 14 arranged on indication surface 22 become visible from the outside.

Indicator 5 may be secured against distal movement with respect to the housing, e.g. movement away from the proximal end as illustrated in FIG. 3. Proximal movement of the indicator 5 with respect to the housing may be allowed.

The number of index elements can be increased in this way, with the size of the index elements and a distance of the index elements of the indication surface being kept constant. More than one turn of index elements is available.

Thus, by rotation of the indicator, indication surface 23 which is not visible from the outside as shown in FIG. 3 can be rotated to be visible from the outside, while the piston rod moves distally away from the proximal end 3.

The indicator 5 can rotate with respect to the housing due to the coupling of piston rod 6 and indicator 5 and move in the proximal direction, thus rotating and translating indication surface 22 under window 15. Rotational movement of the indicator 5 can thus be converted into proximal movement of the indicator 5 along the axis A. Distal movement of the indicator 5 is preferably restricted by mechanical stop 10. Proximal movement of the indicator 5 is preferably restricted by mechanical stop 11. Indication surfaces 13 and 23 may be part of a thread.

Of course, an indicator 5 that has more than one indication surface according to this embodiment or the embodiment to be described next can be implemented in the other drive assemblies described herein above and below.

Figure 4:
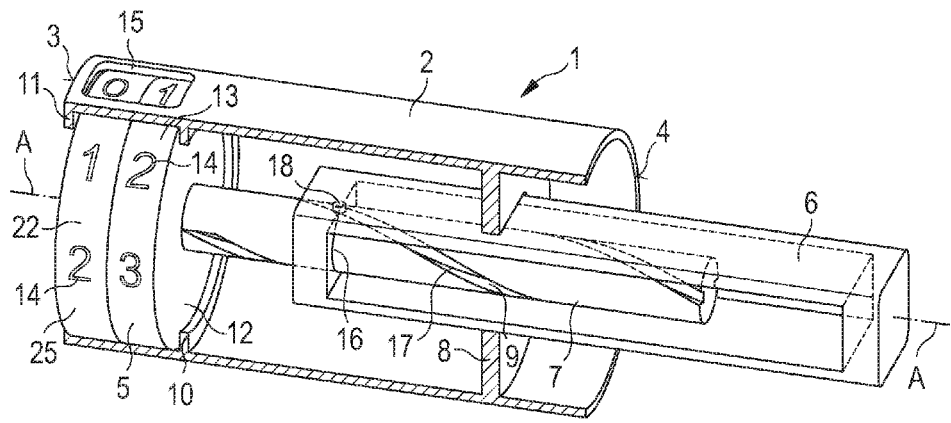
FIG. 4 shows an oblique sectional view of a fourth embodiment of the drive assembly.

FIG. 4 shows an oblique sectional view of a fourth embodiment of the drive assembly 1. The drive assembly shown in FIG. 4 essentially corresponded to the one described in conjunction with FIG. 3.

In contrast thereto, indicator 5 comprises two indicator parts 12 and 25 which can be rotated with respect to one another. Indicator part 12 can comprise indication surface 13. Indicator part 25 can comprise indication surface 22. Both indication surfaces 13 and 22 are visible from the outside through window 15.

Indication surfaces 22 and 13 are rotatable relative to one another. Indicator parts 12 and 25 may be coupled to one another via an odometer(-like) mechanism. A rotation by a predetermined angle, for example a full rotation about 360°, of indicator part 12 relative to indicator part 25 may cause indicator part 25 to rotate, preferably about an angle smaller than the predetermined angle, such that the next index element 14 of indication surface 22 is rotated into indication position.

In this way, the amount of states that can be indicated is considerably increased due to different combinations of index elements on indication surface 22 and index elements on indication surface 13. In particular, numbers having more than one digit, e.g. from 00 to 99, can be displayed easily visible. Indication surface 22 can display the tens and indication surface 13 the units.

Figure 5:
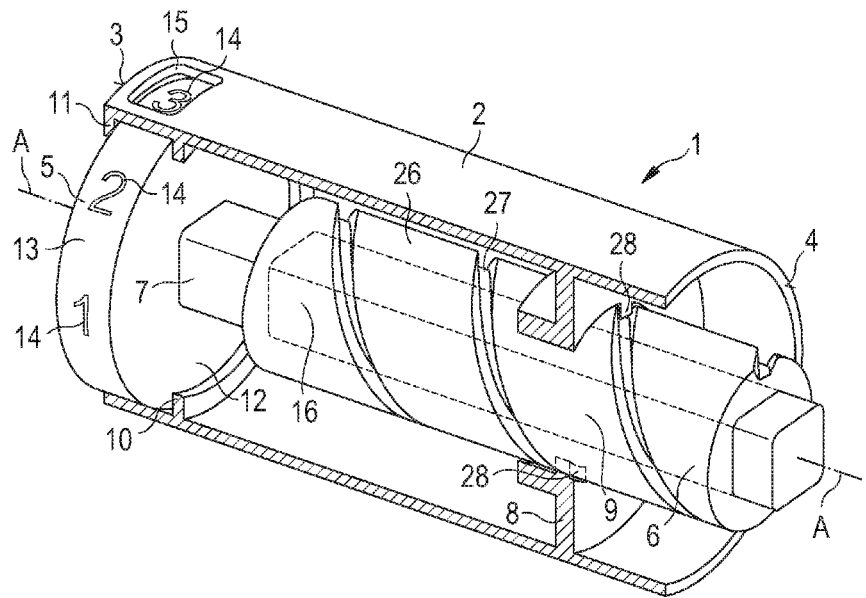
FIG. 5 shows an oblique sectional view of a fifth embodiment of the drive assembly.

FIG. 5 shows an oblique sectional view of a fifth embodiment of the drive assembly 1. The drive assembly according to FIG. 5 essentially corresponds to the one described in connection with FIGS. 1 and 1A.

In contrast to the latter embodiment, the drive assembly according to FIG. 5 is configured for the piston rod 6 to be moved along axis A and to be rotated around axis A with respect to housing 2. Piston rod 6 is threadedly coupled to the housing 2. Preferably, piston rod 6 threadedly engages housing 2.

An outer wall 26 of the piston rod 6 may comprise a (helical) thread 27 (male or female) that engages a thread 28 (female or male, respectively) that is provided within housing 2. Thread 28 and/or 27 may be a part of a thread or a full thread.

Mechanical support 8 may comprise thread 28, for example. Rotation member 7 is coupled to piston rod 6 by a splined connection. In particular, rotation member 7 follows rotation of the piston rod. Thus, the amount, e.g. the angle, by which indicator 5 rotates is equal to the amount piston rod 6 rotates. In particular, in this embodiment rotational movement of the piston rod 6 with respect to the housing is converted into rotational movement of the indicator 5 with respect to the housing 2.

Figure 6:
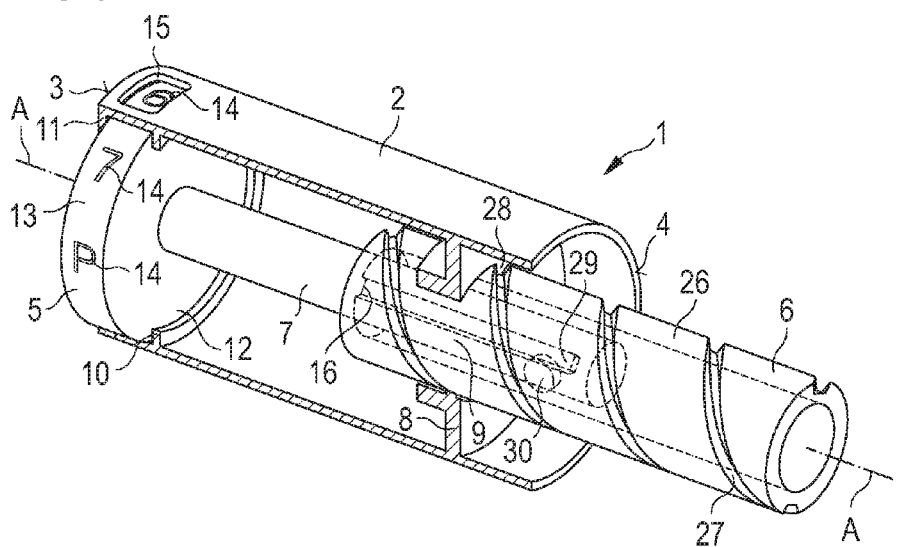
FIG. 6 shows an oblique sectional view of a sixth embodiment of the drive assembly.
Figure 6A:
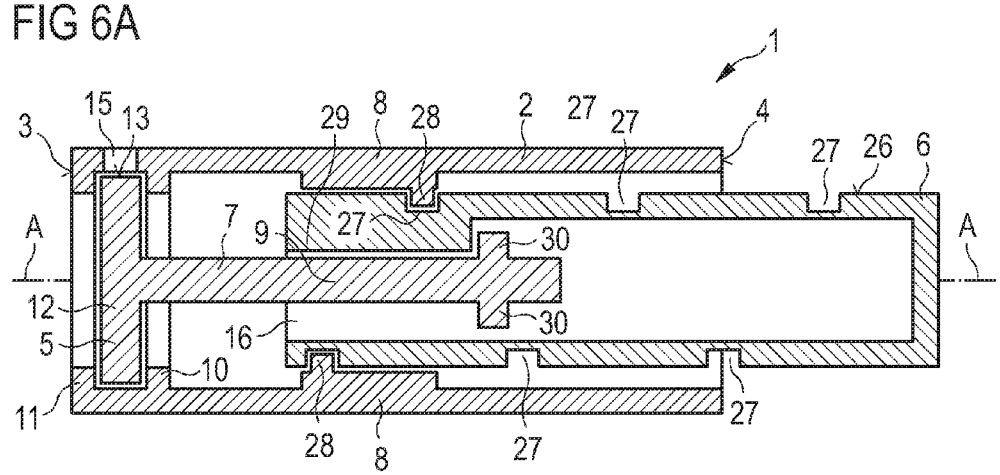
FIG. 6A shows a sectional view of the sixth embodiment with a different position of the piston rod relative to the rotation member.

FIG. 6 shows an oblique sectional view of a sixth embodiment of the drive assembly 1. FIG. 6A shows a sectional view of the sixth embodiment with a different position of the piston rod relative to the rotation member. This embodiment essential corresponds to the one described conjunction with FIG. 5. In particular, piston rod 6 rotates and translates distally along the axis A away from the proximal end 3.

In contrast to the embodiment described in conjunction with FIG. 5, the indicator 5 is decoupled from movement of the piston rod 6 along the axis in a region. That is to say, in this region the piston rod 6 can move along the axis A and along the rotation member 7, without causing indicator 5 to rotate. In other words, the piston rod 6 can move distally along the axis A relative to the indicator 5 without interacting with rotation member 7. In particular, if piston rod and indicator are decoupled, piston rod 6 and rotation member 7 do not interact mechanically. Preferably, there is no mechanical coupling between piston rod 6 and indicator 5 in the region of decoupling.

A piston rod 6 which is decoupled from rotation member 7 is shown in FIG. 6A. Piston rod 6 can rotate and translate independently from indicator 5. No rotation of the indicator 5 is caused. When doses are set and dispensed from a drug delivery device comprising a drive assembly of this kind, indicator 5 does not rotate with respect to the housing 2 while the piston rod 6 moves over a region of the rotation member 7. The drive member of the drive assembly (not explicitly shown) may be moved in the proximal direction away from the housing for setting a dose and in the distal direction towards the housing for dispensing a dose.

For coupling piston rod 6 and indicator 5, the piston rod 6 comprises preferably one or a plurality of protrusions 29, e.g.

a peg, a knob, a lug or a pin. Rotation member 7 may comprise one or a plurality of protrusions 30.

The protrusion 29 can protrude from an inner wall of the piston rod 6. The protrusion 29 extends in a section along the axis which corresponds to a section, in which a rotation of the indicator is desired. The protrusion 29 can be a splined feature, for example a rib, extending along the axis A. Protrusion 29 may be elongated. Protrusion 30 can cause a region of a rotation member to have an enlarged cross section. Protrusion 29 expediently extends from the side of the piston rod 6 that faces the proximal end 3 along axis A away from the proximal end.

As from the situation illustrated in FIG. 6A the piston rod 6 rotates and translates distally away from proximal end 3, mechanical interaction between protrusions 30 and 29 is established (cf. FIG. 6), e.g. by mechanical contact of protrusions 29 and 30. A splined connection between piston rod 6 and rotation member is established and the indicator rotates. Rotation of the indicator follows rotation of the piston rod. In particular, piston rod and indicator rotate by the same angle. Thus, rotational movement of the piston rod 6 with respect to the housing 2 is converted into rotational movement of the indicator 5 with respect to the housing 2. When from the situation shown in FIG. 6A, further doses are dispensed from the drug delivery device, the indicator rotates.

A drive assembly of this kind can be used to count down just the last few doses of a drug available in a drug delivery device, for example. The number of different index elements which has to be provided for can be reduced in this way. Provision of just one indication surface is thus facilitated.

FIG. 7 shows an oblique sectional view of a seventh embodiment of the drive assembly 1. This embodiment essentially corresponds to the one described in conjunction with FIG. 5. In contrast thereto, the indicator 5 may be moveable along the axis A with respect to the housing and/or with respect to the piston rod 6. In particular, the indicator 5 may be moved away from the distal end 4 and/or away from the proximal end 3.

In contrast to the embodiment described in conjunction with FIG. 5, in this embodiment, a drive member 31 of the drive assembly is explicitly shown. The drive member 31, e.g. a drive sleeve, is movable along the axis. Drive member 31 is preferably secured against rotation with respect to the housing 2. The drive member is arranged on the side of the proximal end 3.

Indicator 5 is coupled to the drive member 31 such that it follows movement of the drive member along the axis A. Indicator 5 according to this embodiment can thus be moved along the axis with respect to piston rod 6 and/or housing 2.

Unintentional rotational movement of the indicator 5, for example caused by vibrations, can be prevented. For this purpose, a detent spring (not explicitly shown) can be provided that prevents rotational movement of the indicator 5 with respect to the housing and/or the drive member, which is not caused by translational movement of indicator and piston rod with respect to one another and/or by translational movement of the piston rod with respect to the housing.

Indicator part 12 is retained in the drive member. Indicator 5 is secured against movement along the axis with respect to drive member 31. Alternatively, indicator 5 may be secured against axial movement relative to the housing 2 (not explicitly shown). In this case indicator 5 would be decoupled from movement of the drive member 31.

The indicator 5 may be coupled to drive member 31 by a mechanical stop 32, e.g. a notch, for example, in which the indicator 5, in particular indicator part 12, can be arranged. Indication surface 13 is preferably visible from the outside through the drive member 31. A window 33 may be provided in drive member 31 for this purpose.

For setting of a dose, drive member 31 and indicator 5 may be moved proximally with respect to the piston rod 6 and, in particular, with respect to the housing 2. The piston rod preferably does not move during dose setting. For drug delivery (dose dispense), drive member 31 and indicator may be moved distally with respect to the piston rod 6 and, in particular, with respect to the housing 2. This movement of the drive member 31 may transfer a force to the piston rod 6, causing the piston rod 6 to translate in the distal direction and thus causing the indicator 5 to rotate. Indicator 5 follows rotational movement of the piston rod 6. Thus, rotational movement of the piston rod 6 with respect to the housing 2 is converted into rotational movement of the indicator 5. Rotation member 7 is preferably coupled to the piston rod 6 via a splined connection.

FIG. 8 shows an oblique sectional view of an eighth embodiment of the drive assembly 1. This embodiment essentially corresponds to the one described in conjunction with FIGS. 6 and 6A. In contrast thereto, the indicator 5 is moveable along the axis A with respect to the housing and with respect to the piston rod 6. Drive member 31 is provided for as described in connection with FIG. 7. Indicator 5 can follow movement of the drive member 31 along the axis A away from and towards distal end 4. Coupling between rotation member 7 and piston rod 6 can be effected as described in conjunction with FIGS. 6 and 6A.

For setting a dose, drive member 31 and indicator 5 are moved proximally in the axial direction. The piston rod 6 preferably does not move. The indicator preferably does not rotate with respect to the housing and/or the drive member. For dose delivery (dose dispensing), the drive member may be moved in the distal direction, e.g. towards the housing 2. The movement of the drive member transfers force to the piston rod 6, which moves in the distal direction caused by the force. This distal movement of the piston rod 6, which is coupled to the indicator 5, causes the indicator 5 to rotate (only) if protrusions 30 and 29 interact mechanically, e.g. by mechanical contact.

Figure 9:
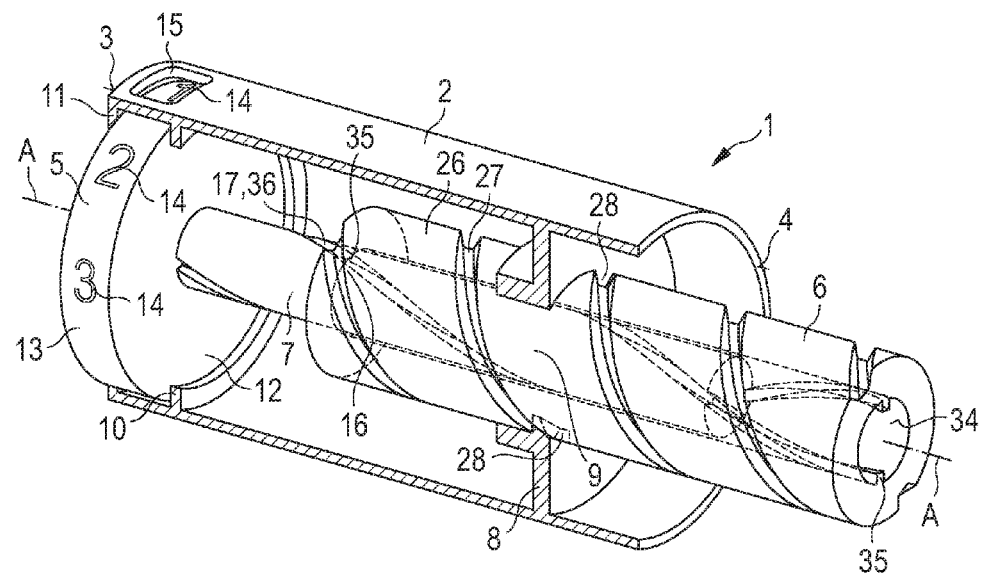
FIG. 9 shows an oblique sectional view of a ninth embodiment of the drive assembly.

FIG. 9 shows an oblique sectional view of a ninth embodiment of the drive assembly 1. This embodiment essentially corresponds to the one described in conjunction with FIG. 5. In contrast thereto, piston rod 6 and rotation member 7 are coupled to one another with relative rotational movement of piston rod 6 and rotation member 7 being allowed.

The rotation member 7 is threadedly engaged to the piston rod 6, preferably by means of a female thread engaging a male thread. The respective thread is preferably a helical thread. The piston rod 6 can comprise a (male) thread 35 arranged on the inner wall 34 of the piston rod 6, for example in the region of opening 16 through which the rotation member 7 extends. The outer surface of the rotation member 7 can comprise a (female) thread 36. Thread 36 can be provided for by indentation 17, for example.

Piston rod 6 is threadedly coupled to housing 2 via (female) thread 27. Piston rod 6 is preferably threadedly engaged to housing 2.

A pitch of the thread 36 for the threaded coupling between piston rod 6 and rotation member 7 can be different from a pitch of thread 27 for the threaded coupling between piston rod 6 and housing 2. The pitch of thread 36 may be wider or narrower than the pitch of thread 36. Rotation angles of piston rod 6 and indicator 5 can thus be different. The amount of rotation of the indicator 5 can be adjusted separately from the amount of rotation of the piston rod 6 by designing these pitches appropriately with respect to each other. The pitches referenced above can have the same hand or opposite hands. The pitches may have different angles with respect to the axis A.

According to FIG. 9 the pitch of thread 36 is wider than the one of thread 27, for example. The angle that thread 36 includes with axis A when viewed in projection onto a plane comprising axis A is smaller than the angle thread 27 includes with axis A when viewed in projection onto the plane.

The threaded coupling of piston rod 6 and rotation member 7 has a higher lead than the threaded coupling of piston rod and housing 2. The threads 27, 36 may have the same sense, for example both clockwise. The rotation angle of the indicator 5 with respect to the housing 2 is smaller than the rotation angle of the piston rod 6 with respect to the housing.

For setting a dose, the drive member may be moved along the axis in the proximal direction, e.g. away from the housing 2. The piston rod 6 does not move during setting. Indicator 5 does not move during setting. For dose delivery (dose dispensing), the drive member may be moved in the distal direction, e.g. towards the housing 2. The movement of the drive member transfers force to the piston rod 6, which moves in the distal direction and rotates around axis A caused by the force. This distal and rotational movement of the piston rod 6, which is coupled to the indicator 5, causes the indicator 5 to rotate. The rotation angles of indicator 5 and piston rod 6 with respect to the housing 2 may be different. Piston rod 6 may drive a piston of a drug cartridge (not explicitly shown) in the distal direction resulting in dispensing a dose of a drug from the cartridge.

If dispensing one of a plurality of doses from a drug delivery device incorporating an according drive assembly 1 requires the piston rod to rotate by a given angle, e.g. ⅓rd turn (120°), and be translated by an according distance, the indicator 5 can rotate by a smaller angle. The number of index elements 14 which can be put into indication position on one indication surface can be increased in this way. Thus indicator 5 can rotate relative to the piston rod, e.g. during dispense of a dose from a drug delivery device.

Figure 10:
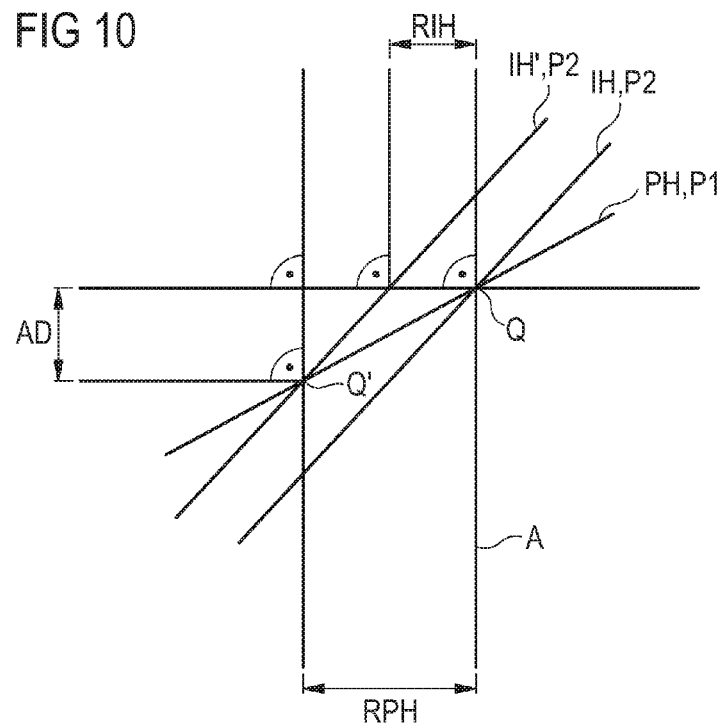
FIG. 10 schematically illustrates the relative movement of piston rod and indicator with respect to one another for a situation similar to the ninth embodiment.

FIG. 10 illustrates the relative movement of piston rod and indicator with respect to one another schematically when indicator and piston rod are threadedly coupled and piston rod and housing are threadedly coupled, similar as discussed in connection with FIG. 9.

As it is illustrated in FIG. 10, when the piston rod rotates and translates through the housing, a representative point Q of the piston rod on the axis A, for example a point on the outer surface of the piston rod, is moved (mapped) along line PH to point Q'. Line PH can represent the angle of the thread for the coupling between housing and piston rod with respect to the axis A, e.g. thread 27 of FIG. 9. This thread has a pitch P1. The piston rod is moved and displaced about an axial displacement AD along the axis A with respect to the housing. The piston rod rotates by RPH with respect to the housing. The pitch of the thread for the threaded coupling of rotation member to piston rod, e.g. thread 36, is P2. Line IH can represent the angle of the thread for the coupling between rotation member and piston rod with respect to axis A. Lines IH and IH' run parallel. The indicator rotates by RIH while the piston rod rotates by RPH. P2 is greater than P1. RIH is less than RPH.

Generally, RIH and RPH are related by:

$$RIH = RPH*(P2-P1)/P2$$

Accordingly, indicator and piston rod can rotate a different amount, e.g. by different angles.

If P2>P1, RIH is less than RPH, if P2 and P1 are in the same direction, i.e. the indicator rotates less than the piston rod, or RIH is greater than RPH, if P2 is oppositely handed with respect to P1 (the opposite hand can be taken into account by inserting —P2 in the equation above), i.e. the indicator rotates more than the piston rod.

If P2<P1, the indicator rotates in a direction opposite to the direction in which the piston rod rotates. In the picture of FIG. 10 opposite handed rotation of indicator with respect to piston rod would be to the right side of axis A.

Figure 11:
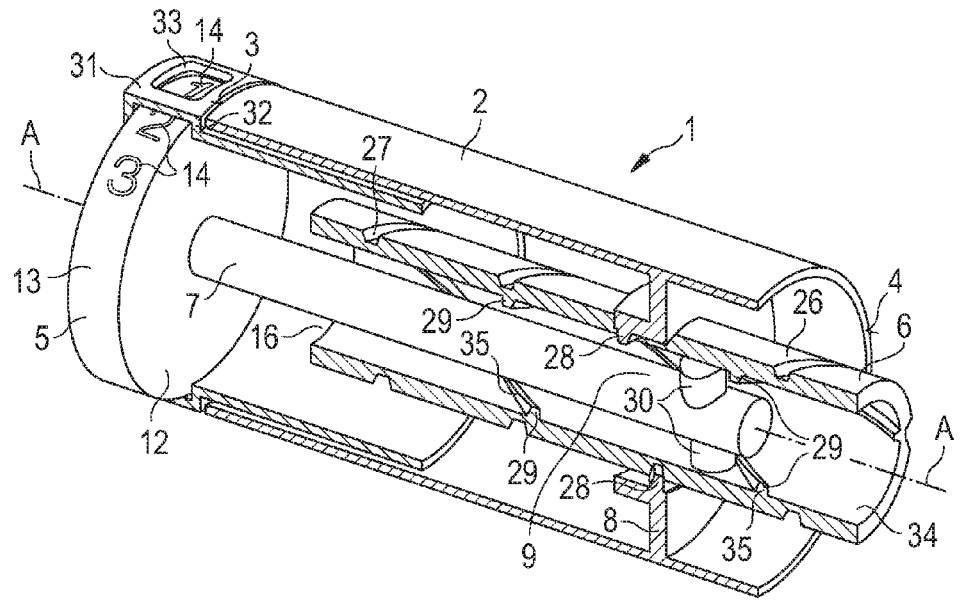
FIG. 11 shows a sectional view of a tenth embodiment of the drive assembly in a first, starting position.
Figure 11A:
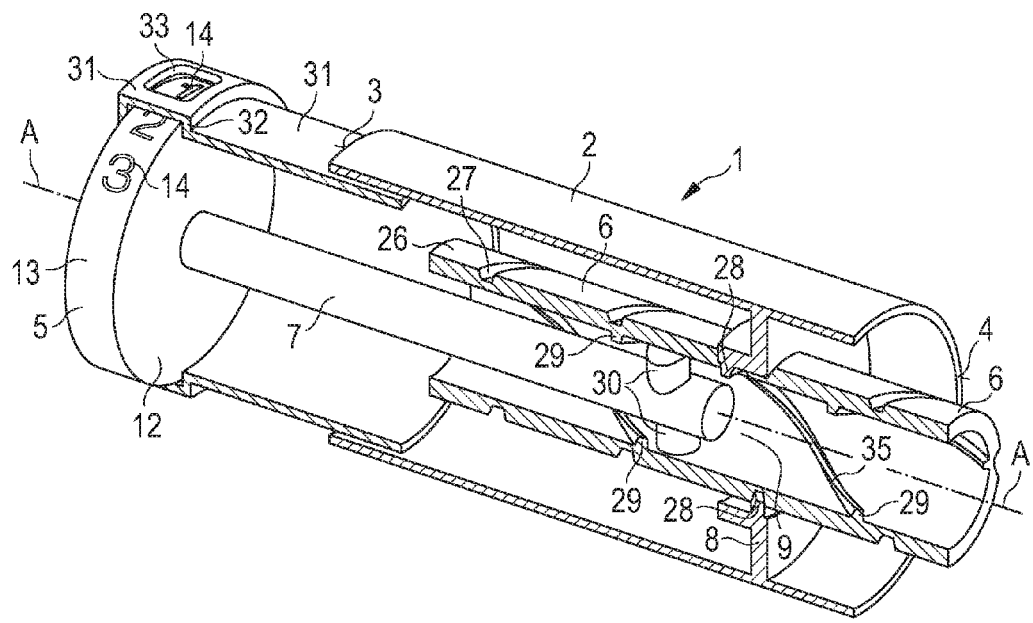
FIG. 11A shows a sectional view of the tenth embodiment in a second, e.g. dose set, position.
Figure 11B:
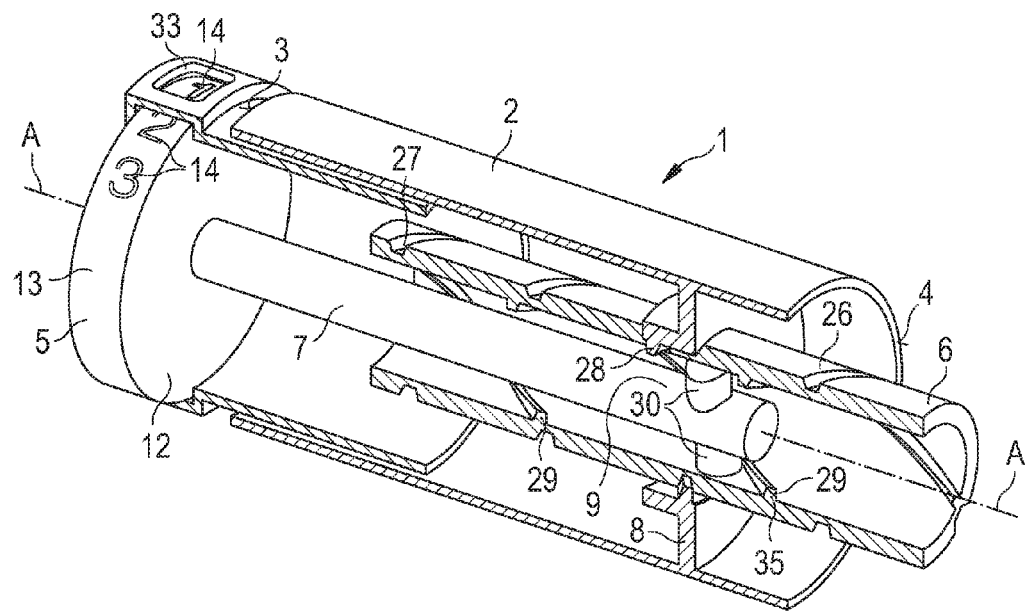
FIG. 11B shows a sectional view of the tenth embodiment in a third, e.g. dose dispensed, position.
Figure 11C:
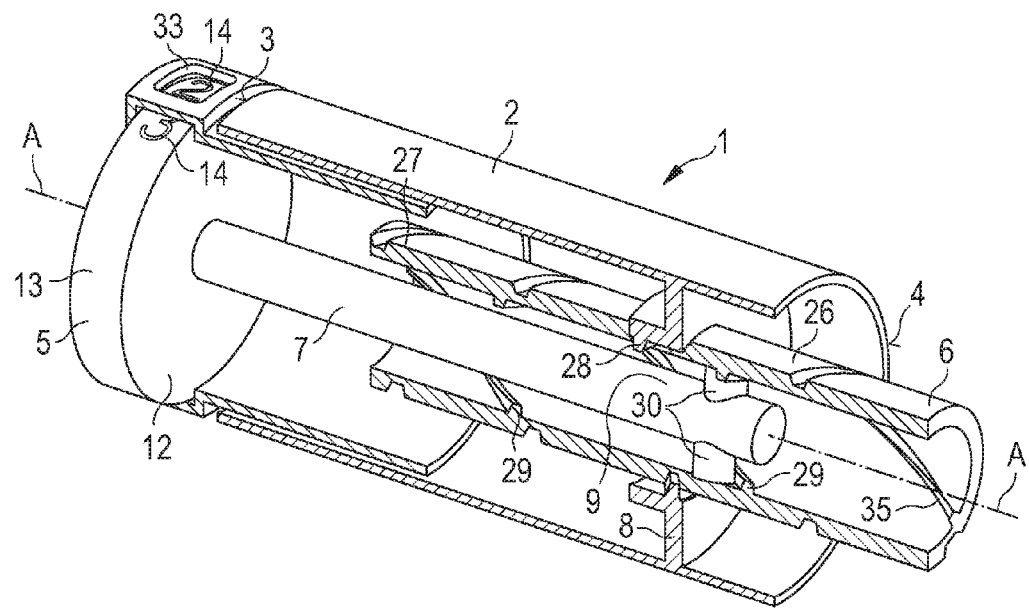
FIG. 11C shows a sectional view of the tenth embodiment in a third, e.g. indicator rotated, position.

FIG. 11 shows a sectional view of a tenth embodiment of the drive assembly in a first, starting position. FIG. 11A shows a sectional view of the tenth embodiment in a second, e.g. dose set, position. FIG. 11B shows a sectional view of the tenth embodiment in a third, e.g. dose partly dispensed, position. FIG. 11C shows a sectional view of the tenth embodiment in a third, e.g. indicator rotated, position.

This embodiment essentially corresponds to the ones described in connection with FIGS. 7 and 8. In particular, indicator 5 is movable with respect to piston rod 6 and with respect to housing 2 along axis A.

Indicator 5 is coupled to drive member 31. Indicator 5 is secured against movement along axis A relative to drive member 31. This relative movement may be prevented by a mechanical stop 32, e.g. a notch, of the drive member 31, in which the indicator 5 may be arranged. Indicator 5 follows movement of the drive member 31 along axis A. Piston rod 6 is movable distally along axis A and rotatable around axis A.

A partial region of rotation member 7 is arranged within piston rod 6, e.g. within a cavity of the piston rod 6. Rotation member 7 has a protrusion 30, preferably a plurality of protrusions 30. The respective protrusion 30 can be formed unitary with the rotation member or as a discrete element connected to the rotation member. Two protrusions 30 may be disposed oppositely with respect to each other. Two protrusions 30 may be aligned along a straight line running obliquely or perpendicularly to axis A. The respective protrusion 30 may protrude radially, i.e. perpendicular to axis A, from the rotation member 7. The respective protrusion 30 can be arranged in the region of the distal end or at the distal end of the rotation member 7. The respective protrusion 30 may be a peg, a knob, a lug or a pin, for example. Alternatively, the respective protrusion 30 may be a part of a thread or a full thread (not explicitly shown).

Within the piston rod 6 are provided one or a plurality of protrusions 29. The respective protrusion may protrude from inner wall 34 of the piston rod 6. The respective protrusion 29 can be formed unitary with the piston rod or as a discrete element connected to the piston rod 6. The separate protrusions 29 shown can be part of a single (male) thread 35. Thread 35 may be a helical thread.

Rotation member 7 can be moved freely along the axis A in the area between two adjacent protrusions 29, i.e. without the rotation member being caused to rotate due to interaction with the piston rod 6. The distance by which the rotation member 7 can be moved freely along the axis A with respect to the piston rod 6 can correspond to or be determined by the distance between adjacent protrusions 29, for example by the width of the thread 35. Thread 35 may be a slack thread, i.e. a thread having a counterpart not (tightly) engaged to it, like rotation member 7, for example. Protrusions 29 are preferably adapted to limit the distance about which the rotation member 7 can be moved with respect to the piston rod 6 without interacting with one of protrusions 29.

Protrusions 29 and 30 can be configured to be able to mechanically contact each other when the rotation member and the piston rod are moved relative to one another along axis A and/or when piston rod 6 is moved away from the proximal end 3, e.g. for a drug-dispense process.

The respective protrusion 30 of the rotation member 7 can be in mechanical contact with the piston rod 6, in particular the inner wall 34 thereof, or arranged at a distance from the inner wall that is less than a height of the protrusion 29 with respect to inner wall 34.

The relative movement of indicator 5 to piston rod 6 for the different positions shown in FIGS. 11, 11A, 11B and 11C is illustrated schematically in FIG. 12 and explained in connection therewith. The illustration in FIG. 12 is similar to the one of FIG. 10.

Starting from the position shown in FIG. 11, the rotation member is moved away from the distal end 4 and, in particular, away from the proximal end 3 of housing 2, for example by moving the drive member 31 proximally accordingly. Mechanical contact of protrusions 29 and 30 is expediently avoided (cf. FIG. 11A). Therefore, rotation member 7 does not rotate. This axial movement of the rotation member can correspond to the setting of a dose of a drug, e.g. by a user of a drug delivery device. The distance between adjacent protrusions 29 is preferably chosen such as to allow relative movement of the indicator 5 with respect to piston rod 6 by a predetermined distance without causing piston rod 6 and/or rotation member 7 to rotate due to interaction of piston rod 6 and rotation member 7. This predetermined distance may correspond to the distance the drive member 31 has to be moved for setting a dose. In the picture of FIG. 12 protrusion 30 is moved along axis A from position S1 to S2 correspondingly.

Thereafter, rotation member 7 is moved axially towards the distal end 4 of the housing 2 (cf. FIG. 11B) together with the indicator 5 and the drive member 31. The kinetic energy transferred by this movement can be used for moving the piston rod 6 distally away from the proximal end 3, e.g. for dispensing a drug from a drug delivery device. During the first portion of the distance of the movement of the rotation member 7 towards distal end 4, the rotation member 7 is decoupled from the piston rod. There is no rotational movement of the rotation member relative to the housing when the rotation member is moved in the first portion along axis A towards distal end 4, i.e. from S2 to S3 in FIG. 12.

Hence, the dose to be administered can be partially dispensed before the indicator 5 rotates, because the piston rod 6 can translate and rotate freely for dispensing the dose with respect to the rotation member 7 over a certain distance, for example by less than the width of thread 35. The width of thread 35 or the distance between adjacent protrusions is represented by WT in FIG. 12.

In the position shown in FIG. 11B, protrusion 30 preferably mechanically contacts protrusion 29 which distally restricts the distance which the rotation member 7 can travel freely.

Thus, in a second portion of the movement of the rotation member 7 towards the distal end 4, rotation of the rotation member is effected, FIG. 11C. Protrusion(s) 30 is (are) guided along protrusion 29 by mechanical interaction of protrusions 29 and 30 which results in a rotation of the rotation member 7 around axis A. The indicator 5 is caused to rotate in this way. Thus, rotational and translational movement of the piston rod 6 with respect to the housing is converted into rotational movement of the indicator 5 with respect to the housing 2 and/or with respect to the piston rod 6. The next index element 14 in line can be rotated into indication position, for example under window 33 of drive member 31. In FIG. 12, rotation of the rotation member 7, which is caused by rotation and translation of the piston rod 6, rotates protrusion 30 into position S4. As far as the axial component of the position is concerned position S4 corresponds to position S1.

The remaining, not described elements of FIG. 12 correspond to the ones of FIG. 10. Lines IH, IH' and IH" run parallel.

$$\text{Like in FIG. 10, } RIH = RPH*(P2-P1)/P2. \tag{1}$$

The proportion of the distance over which the drive member 31 is moved towards the distal end 5, in which proportion the indicator is rotated, compared to the total distance which the drive member 31 is moved towards the distal end is given by:

$$1/[MechAdv*P1/(P2-P1)+1] \tag{2}$$

Therein, MechAdv is the mechanical advantage. MechAdv can be given by the distance d1 the drive member 31 moves towards the distal end (for dispense of a single dose) compared to, for example divided by, the distance d2 the piston rod moves (during dose dispense of a single dose). Preferably, d1>d2. d2 can be given by axial displacement AD. MechAdv may be 1 (1:1) or greater than 1, preferably greater than or equal 2 (2:1). It is particularly preferred for MechAdv to be greater than or equal 3 (3:1). Drive assemblies described above and below may also be configured with a mechanical advantage of this kind.

Let us assume the piston rod 6 rotates a first amount, e.g. $1/3^{rd}$ turn, i.e. 120°, for delivering a single dose. If it is desired for the indicator to rotate a second amount, which may be smaller than the first one, e.g. $1/9^{th}$ turn, i.e. 40°, it follows from equation (1) that $P1=2/3*P2$.

If MechAdv is 3, it follows from equation (2) that the proportion of the total distance the drive member travels towards the distal end, in which the indicator rotates, is $1/(3*2+1)=1/7$. Thus, if the drive member travels 17.5 mm in total, the indicator rotates during the final 2.5 mm.

Therefore, rotation of the indicator may take place not until near the end of a dose-dispense sequence.

In contrast to embodiments which rotate indicator and piston rod simultaneously and where is no decoupling of the indicator from rotational movement of the piston rod for a portion of the movement of the piston rod along the axis, the present embodiment facilitates providing a drug delivery device which provides a user with an audible or visual feedback that the dose is completed, preferably for each dose to be dispensed. Feedback can be given by coupling a feedback member (not explicitly shown) to the indicator, said feedback member being activated by the rotation of the indicator. The rotation of the indicator preferably takes place not until near the end of the dispension of a single dose as described above.

Drug delivery devices suitable for incorporating a drive assembly as described above and further features related to the drive assembly are described below in connection with FIGS. 13 to 14.

Figure 13:
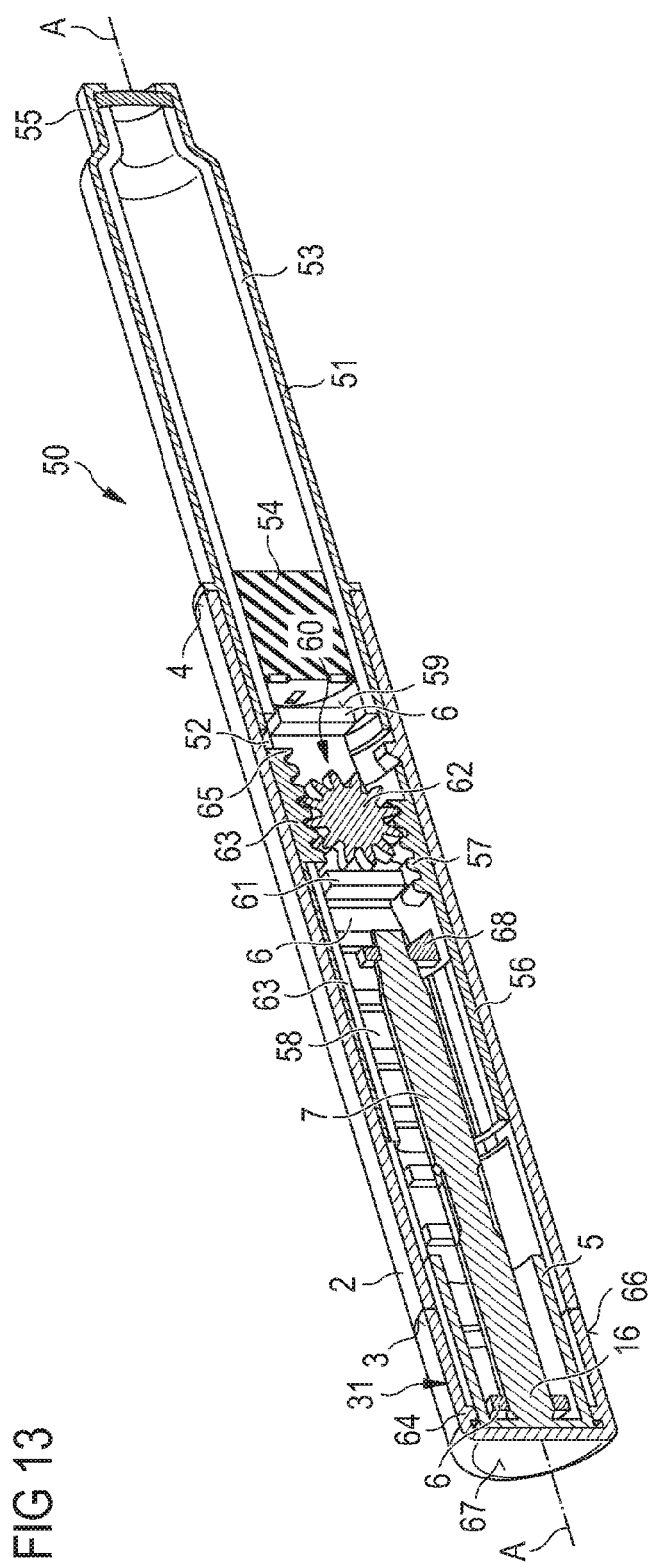
FIG. 13 shows an oblique sectional view of a first embodiment of a drug delivery device.
Figure 13D:
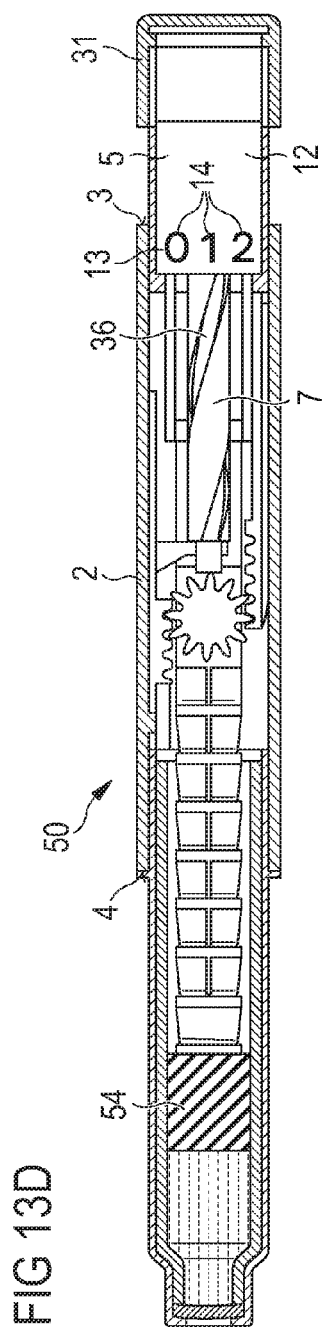
FIG. 13D shows a sectional view of the first embodiment of the drug delivery device in a fourth, e.g. final dose set, position.
Figure 13E:
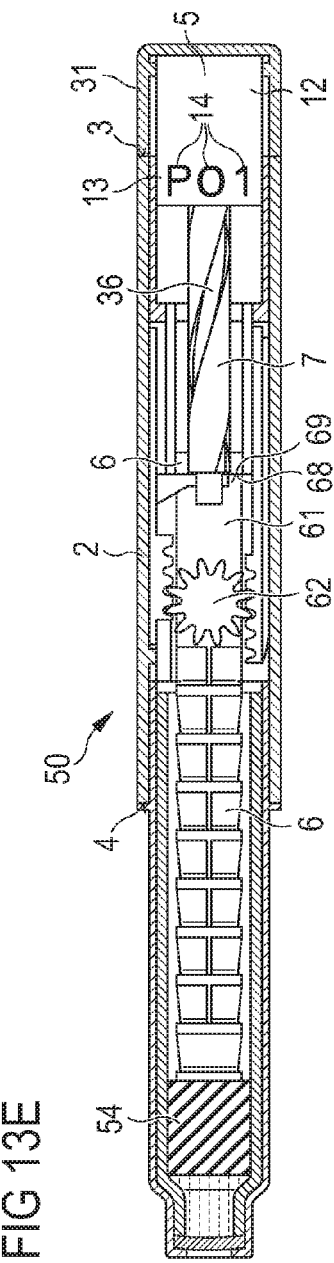
FIG. 13E shows a sectional view of the first embodiment of the drug delivery device in a fifth, e.g. final dose dispensed, position.

FIG. 13 shows an oblique sectional view of a first embodiment of a drug delivery device. FIG. 13A shows a side view of the first embodiment of the drug delivery device in a first, e.g. cartridge full, position. FIG. 13B shows a sectional view of the first embodiment of the drug delivery device in a second, e.g. first dose set, position. FIG. 13C shows a sectional view of the first embodiment of the drug delivery device in a third, e.g. first dose dispensed, position. FIG. 13D shows a sectional view of the first embodiment of the drug delivery device in a fourth, e.g. final dose set, position. FIG. 13E shows a sectional view of the first embodiment of the drug delivery device in a fifth, e.g. final dose dispensed, position.

The drug delivery device 50 comprises a cartridge retaining part 51, and a main (exterior) housing part 2. The proximal end 52 of the cartridge retaining part 51 and the distal end 4 of the main housing 2 are secured together by any suitable means known to the person skilled in the art. In the illustrated embodiment, the cartridge retaining part 51 is secured within the distal end 4 of the main housing part 2.

A cartridge 53 from which a number of doses of a medicinal product may be dispensed is provided in the cartridge retaining part 51. The medicinal product may be one of the ones described further above, for example. A piston 54 is retained in the proximal end of the cartridge 53.

A removable cap may be releasably retained over the distal end 55 of the cartridge retaining part 51 (not explicitly shown). The removable cap may be optionally provided with one or more window apertures through which the position of the piston 54 within the cartridge 53 can be viewed.

The distal end 55 of the cartridge retaining part 51 may be provided with a distal threaded region (not explicitly shown). This region may be designed for the attachment of a suitable needle assembly to enable medicament to be dispensed from the cartridge 53.

In the illustrated embodiment, the main housing part 2 is provided with an internal housing 56. The internal housing 56 is secured against rotational and/or axial movement with respect to the main housing part 2. The internal housing 56 is provided with a rack 57 extending along the main axis A of the internal housing 56. Alternatively, the internal housing 56 may be formed integrally with the main housing part 2. Additionally, the internal housing 56 may be provided with a plurality of guide lugs (not shown) and/or pawl means (not shown). The pawl means may be an integrated part of the internal housing 56 or may be a separate component as illustrated.

A piston rod 6 extending through the main housing 2 has a first set of indentations (not explicitly shown) extending longitudinally along external surfaces of the piston rod 6. A second set of indentations 58 extend longitudinally along internal surfaces of the piston rod 6. The first set of indentations of the piston rod 6 extend through and are engaged with the pawl means of the internal housing 56 to prevent movement of the piston rod 6 in the proximal direction during setting of the device. A bearing surface 59 located at the distal end of the piston rod 6 is disposed to mechanically contact, preferably to abut, the proximal face of the piston 54. In the illustrated embodiment the longitudinal spacing of the first set of indentations and the second set of indentations 58 is essentially equal.

A gear 60, comprising or consisting of a carrier 61 and/or a gear wheel 62, said gear wheel being free to rotate within the carrier 61, is located within a channel within the piston rod 6. Pawl arms located on the carrier 61 are releasably engaged with the second set of indentations 58 of the piston rod 6 (not explicitly shown). The pawl arms of the carrier 61 are designed to transmit force to the piston rod 6 in the distal direction during dispense and to allow relative movement between the gear 60 and the piston rod 6 in the proximal direction during setting. The teeth of the gear wheel 62 are permanently engaged with the teeth of the rack 57 of the internal housing 56.

A drive member 31 extends about the piston rod 6. The drive member 31 comprises a rack part 63 and an activation part 64. The rack part 63 and the activation part 64 are secured to each other to prevent rotational and/or axial movement there between. Alternatively, the drive member 31 may be a unitary component consisting of an integrated rack part 63 and activation part 64.

The rack part 63 is provided with a rack 65 extending along the main axis of the rack part 63. The teeth of the rack 65 of the rack part 63 are permanently engaged with the teeth of the gear wheel 62.

The drive member 31 has a plurality of guide slots (not shown) in which the guide lugs (not shown) of the internal housing 56 are located. These guide slots define the extent of permissible axial movement of the drive member 31 with respect to the housing part 2. In the illustrated embodiment the guide slots also prevent rotational movement of the drive member 31 relative to the main housing part 2.

The activation part 64 of the drive member 31 has a plurality of grip surfaces 66 and a dispensing face 67.

The drug delivery device 50 comprises an indicator 5 and a rotation member 7 as described further above in connection with the previous embodiments relating to the drive assembly. The indicator 5 is rotatable with respect to piston rod 6 and main housing part 2 around axis A. Piston rod 6 is movable along axis A in the distal direction. Indicator 5 is coupled to piston rod 6. Indicator 5 may rotate as the piston rod moves in the distal direction. The rotation member 7 may be threadedly engaged to the piston rod 6, for example by a threaded engagement in the region of opening 16 in the piston rod 6, through which the rotation member 7 extends. A thread—e.g. a full or a part thread—may be provided for in opening 16 for the threaded engagement of rotation member 7 and piston rod 6. Rotation member 7 may be a threaded shaft that threads into opening 16. Opening 16 is arranged on the side of the piston rod 6 that faces the proximal end 4. Rotation member 7 may be threaded all the way (cf. thread 36 in FIGS. 13A to 13E). The respective thread of the opening or the rotation member is preferably a helical thread (full or part thread, male thread or female thread, respectively). The indicator 5 is secured against relative movement to the housing part 2 along axis A.

Rotation member 7 may be supported by mechanical support 68 against displacement in the radial direction with respect to axis A. Mechanical support 68 may be arranged on or be formed unitary with internal housing 56. Mechanical support 68 may correspond to the mechanical supports described further above.

Operation of the drug delivery device will now be described.

In starting position, with no dose dispensed, an index element 14, for example indicating that the prime dose is still available, like letter P, is visible in indication position through window 15 in housing part 2 from the outside, FIG. 13A.

To set a dose a user grips the grip surfaces 66 of the drive member 31. The user then pulls the drive member 31 in a proximal direction away from the main housing part 2 thereby moving the rack part 63 in a proximal direction.

The proximal movement of the rack part 63 causes the gear wheel 62 to rotate and move proximally by virtue of the engagement of the teeth of the gear wheel 62 of the gear 60 with the teeth of the rack 65 of the rack part 63 and the teeth of the rack 57 of the internal housing 56 thus moving the gear 60 in the proximal direction, FIG. 13B. The indicator 5 does not rotate during this movement.

The piston rod 6 is prevented from moving proximally by interaction of pawl means of the internal housing 56 with a first set of indentations on the piston rod 6. As the drive member 31 travels in the proximal direction relative to the piston rod 6, the pawl arms of the carrier 61 are displaced inwardly by interaction with the second set of indentations 58 of the piston rod 6.

The proximal travel of the drive member 31 is limited by the guide slots of the rack part 63. At the end of the travel of the drive member 31, the pawl arms of the carrier 61 engage with the next sequential indentation of the second set of indentations 58 of the piston rod 6 as indicated in FIG. 13B. The action of the pawl arms of the carrier 61 positively engaging the second set of indentations 58 of the piston rod 6 creates an audible and tactile feedback to the user to indicate that the dose has been set. The indicator does not rotate during dose setting.

When the dose has been set, the user may then dispense this dose by depressing the dispensing face 67 of the activation part 64 of the drive member 31. By this action the drive member 31 and the rack part 63 are moved axially in the distal direction relative to the main housing part 2, FIG. 13C. As the teeth of the gear wheel 62 of the gear 60 are engaged with the teeth of the rack 65 of the rack part 63 and the teeth of the rack 57 of the internal housing 56, the gear wheel 62 of the gear 60 is caused to rotate and move in the distal direction thus moving the gear 60 longitudinally in the distal direction. As the pawl arms of the carrier 61 of the gear 60 are engaged with the second set of indentations 58 of the piston rod 6, the piston rod 6 is caused to move longitudinally in the distal direction with respect to main housing part 2 and, in particular with respect to the internal housing 56.

The distal axial movement of the piston rod 6 causes the bearing surface 59 of the piston rod 6 to bear against the piston 54 of the cartridge 53. This causes a dose of medicament to be dispensed form the cartridge, e.g. through the needle (not shown), which may be attached distally to the drug delivery device.

The distal travel of the drive member 31 is limited by the guide slots (not shown) of the rack part 63. Audible and tactile feedback to indicate that the dose has been dispensed is provided by the interaction of the pawl means (not shown) of the internal housing 56 with the first set of indentations (not shown) of the piston rod 6.

The coupling between piston rod 6 and rotation member 7 causes the indicator 5 to rotate the next index element 14 in line, e.g. digit "7" in FIG. 13C, into the indication position during the distal axial movement of the piston rod 6. The indicator 5 is adapted to count down the number of doses remaining for dispense.

Further doses may be delivered as required up to a predetermined maximum number of doses. FIGS. 13D and 13E show the setting of the last dose and the dispensing of the last dose from the drug delivery device 50. The mechanism corresponds to the one described above in connection with FIGS. 13A to 13C. The index elements 14 on indication surface 13 rotate one after the other into indication position and preferably count down, e.g. to "0", as dose dispensing proceeds.

FIG. 13E shows the drug delivery device in a condition where the maximum number of doses has been delivered. In this condition the proximal face 68 of the carrier 61 may abut an internal distal face 69 of the piston rod 6 to prevent further axial movement of the gear 60 and thus of the drive member 31 in proximal direction.

Of course, other embodiments of the drive assembly as described above may be implemented in a drug delivery device according to this embodiment. As the piston rod 6 moves purely translational, drive assemblies as described in connection with FIGS. 1 to 4 are particularly suitable to be implemented in a drug delivery device according to this embodiment.

Figure 14:
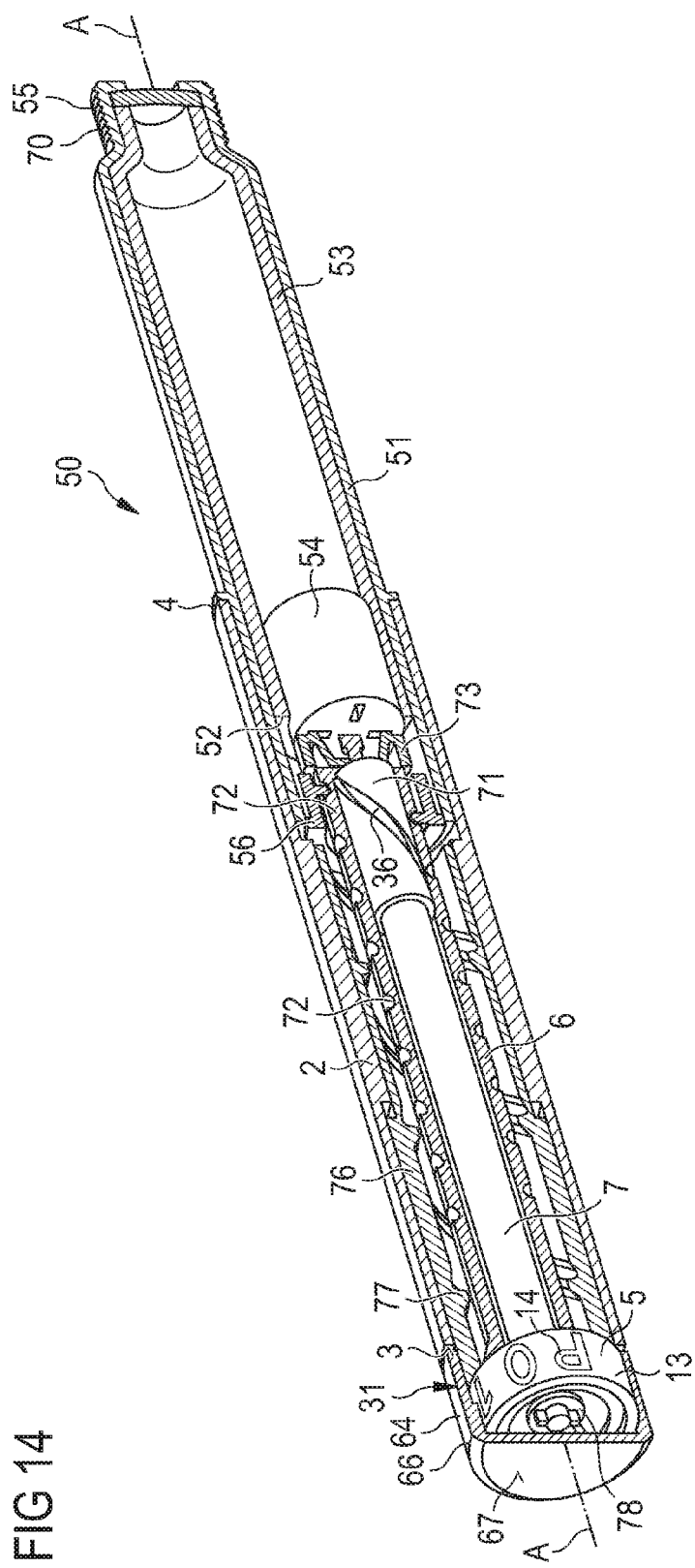
FIG. 14 shows an oblique sectional view of a second embodiment of the drug delivery device.
Figure 14A:
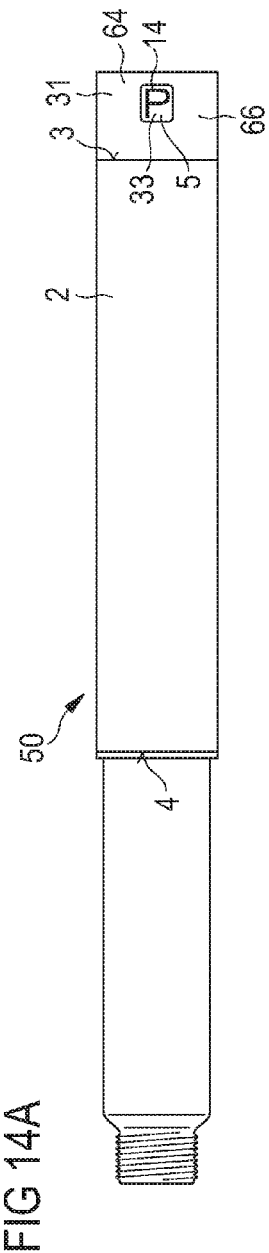
FIG. 14A shows a side view of the second embodiment of the drug delivery device in a first, e.g. cartridge full, position.
Figure 14B:
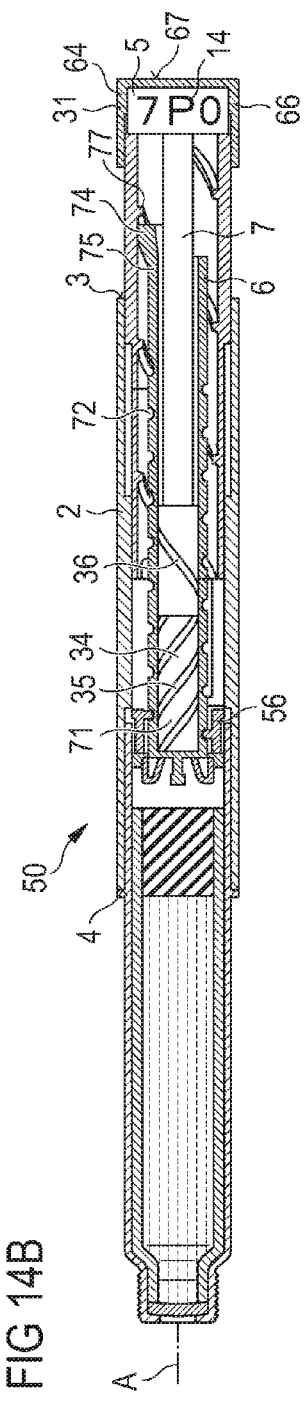
FIG. 14B shows a sectional view of the second embodiment of the drug delivery device in a second, e.g. first dose set, position.
Figure 14C:
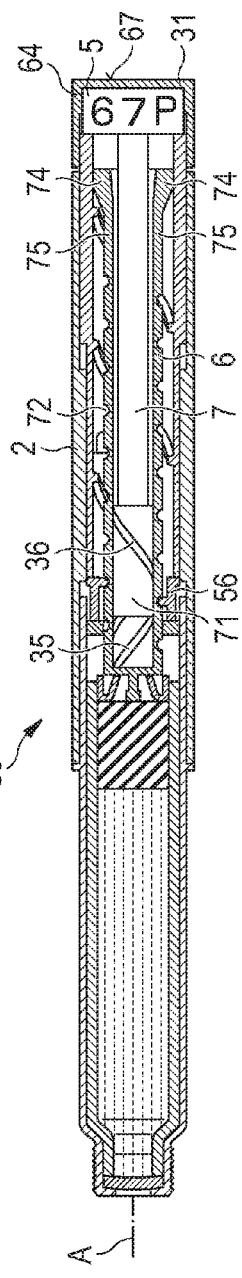
FIG. 14C shows a sectional view of the second embodiment of the drug delivery device in a third, e.g. first dose dispensed, position.
Figure 14D:
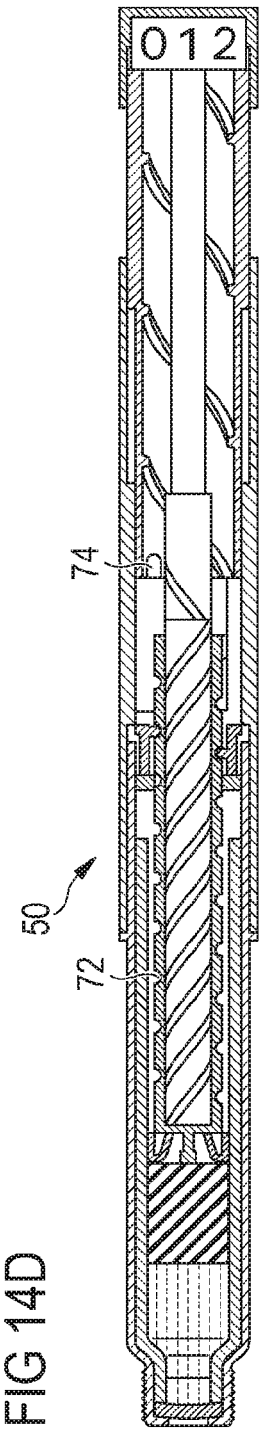
FIG. 14D shows a sectional view of the second embodiment of the drug delivery device in a fourth, e.g. final dose set, position.
Figure 14E:
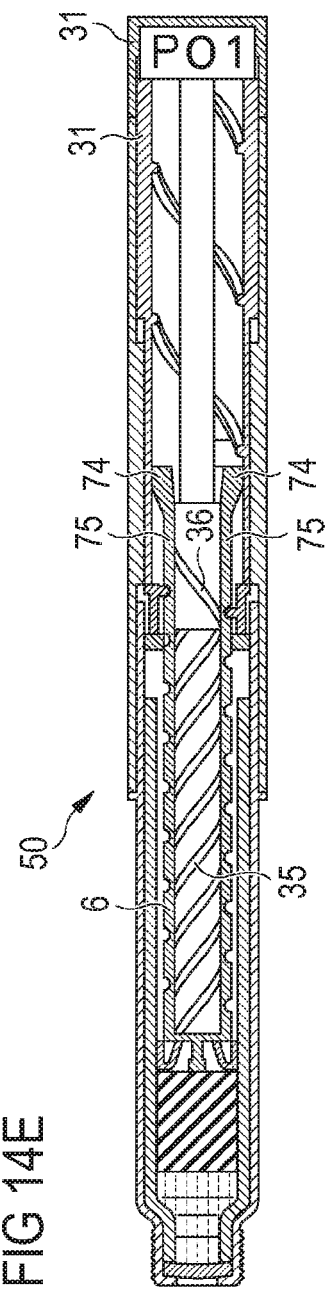
FIG. 14E shows a sectional view of the second embodiment of the drug delivery device in a fifth, e.g. final dose dispensed, position.

FIG. 14 shows an oblique sectional view of a second embodiment of the drug delivery device. FIG. 14A shows a side view of the second embodiment of the drug delivery device in a first, e.g. cartridge full, position. FIG. 14B shows a sectional view of the second embodiment of the drug delivery device in a second, e.g. first dose set, position. FIG. 14C shows a sectional view of the second embodiment of the drug delivery device in a third, e.g. first dose dispensed, position. FIG. 14D shows a sectional view of the second embodiment of the drug delivery device in a fourth, e.g. final dose set, position. FIG. 14E shows a sectional view of the second embodiment of the drug delivery device in a fifth, e.g. final dose dispensed, position.

The drug delivery device 50 comprises a cartridge retaining part 51, and a main (exterior) housing part 2. The proximal end 52 of the cartridge retaining part 51 and the distal end 4 of the main housing 2 are secured together by any suitable means known to the person skilled in the art. In the illustrated embodiment, the cartridge retaining part 51 is secured within the distal end 4 of the main housing part 2.

A cartridge 53 from which a number of doses of a medicinal product may be dispensed is provided in the cartridge retaining part 51. A piston 54 is retained in the proximal end of the cartridge 53.

A removable cap (not shown) can be releasably retained over the distal end 55 of the cartridge retaining part 51. The removable cap is optionally provided with one or more window apertures through which the position of the piston 54 within the cartridge 53 can be viewed.

The distal end 55 of the cartridge retaining part 51 in the illustrated embodiment, is provided with a distal threaded region 70. Threaded region 70 may be designed for the attachment of a suitable needle assembly (not shown). A medicinal product, e.g. a product as described further above, may be dispensed distally from the cartridge 53, for example through the needle.

In the illustrated embodiment, the main housing part 2 is provided with an internal housing 56. The internal housing 56 is secured against rotational and/or axial movement with respect to the main housing part 2. The internal housing 56 is provided with a threaded circular opening 71 extending through the distal end of the internal housing 56. Threaded circular opening 71 may comprise a series of part threads (as it is illustrated) or a complete thread. Alternatively, the internal housing 56 may be formed integrally with the main housing part 2. Additionally, the internal housing 56 may be provided with a plurality of guide slots and pawl means. The internal housing 56 may be formed by the mechanical support described in conjunction with the previous embodiments. Opening 71 may correspond to the opening described previously (cf. support 8 and opening 9 in FIGS. 1 to 12).

A first thread 72 is formed at the distal end of the piston rod 6. The piston rod 6 is of generally circular cross-section. The first thread 72 of the piston rod 6 extends through and is threadedly engaged with the threaded circular opening 71 of the internal housing 56. A pressure foot 73 is located at the distal end of the piston rod 6. The pressure foot 73 is disposed to abut the proximal face of the piston 54. A second thread 74 is formed at the proximal end of the piston rod 6 (cf. FIGS. 14B to 14D). The second thread 74 may comprise a series of part threads (as it is illustrated) or a complete thread. The second thread may be formed on one or a plurality of flexible arms 75 of the piston rod 6.

The first thread 72 and the second thread 74 are oppositely disposed.

In the illustrated embodiment the first thread 72 may be provided with a plurality of features (not shown) that cooperate with the part threads of the threaded circular opening 71 to prevent movement of the piston rod 6 in the proximal direction during setting of the device.

A drive member 31 extends about the piston rod 6. The drive member 31 comprises a threaded part 76, for example of a generally cylindrical cross-section, and an activation part 64. The threaded part 76 and the activation part 64 are secured to each other to prevent rotational and/or axial movement there between. Alternatively, the drive member 31 may be a unitary component comprising or consisting of an integrated threaded part 76 and activation part 64.

In the illustrated embodiment, the threaded part 76 is provided with a longitudinally extending helical thread 77, i.e. a thread extending along axis A, formed on the internal cylindrical surface. The flank of the proximal side of the helical thread 77 is designed to maintain contact with the second thread 74 of the piston rod 6 when dispensing a dose, whilst the flank of the distal side of the helical thread 77 is designed to allow the second thread 74 of the piston rod 6 to disengage when setting a dose. In this way the helical thread 77 of the threaded part 76 is releasably engaged with the second thread 74 of the piston rod 6.

The drive member 31 has a plurality of features formed on the external surface designed to move axially within the guide slots of the internal housing 56. These guide slots define the extent of permissible axial movement of the drive member 31 with respect to the housing part 2. In the illustrated embodiment the guide slots also prevent rotational movement of the drive member 31 relative to the main housing part 2.

The activation part 64 of the drive member 31 has a plurality of grip surfaces 66 and a dispensing face 67.

The drive member 31 is provided with a detent means that is designed to interact with the pawl means of the internal housing 56.

The drug delivery device 50 comprises an indicator 5 and a rotation member 7 as described further above in connection with the previous embodiments relating to the drive assembly. The indicator 5 is rotatable with respect to piston rod 6 and main housing part 2 around axis A. Piston rod 6 is movable along axis A in the distal direction and rotatable around axis A. Indicator 5 is coupleable to piston rod 6. Indicator 5 is coupled to drive member 31. Preferably, the indicator is secured against relative movement of the indicator 5 along the axis A with respect to the drive member 31. Drive member 31 may extend about indication surface 13.

Thread 36, which may be formed by a part thread or a complete thread, is formed on the rotation member 7, preferably unitary with rotation member 7. Thread 36 may be a male or a female thread. Thread 36 is preferably formed in the distal region of the rotation member 7. Thread 36 is preferably a helical thread.

On an inner wall 34 of the piston rod 6 thread 35 is formed, preferably unitary with piston rod 6. Thread 35 may be a male or a female thread. Thread 35 is preferably a helical thread. Preferably the thread type of thread 35, e.g. female, is different from the one of thread 36, e.g. male.

An indicator 5 can be coupled to the piston rod 6 via threads 35 (cf. FIGS. 14B to 14D) and 36 for rotating the indicator.

Rotation member 7 is movable along axis A freely with respect to piston rod 6 in a region, i.e. without causing mechanical contact with the piston rod and/or rotation of the piston rod. Threads 35 and 36 may be configured to leave enough slackness between them for allowing for this movement of the rotation member 7 relative to the piston rod 6. The setting of a dose by moving the drive member 31 and the indicator 5 away from the proximal end 3 is thus facilitated. Thread 35 is preferably wider than thread 36 for this purpose.

Operation of the drug delivery device 50 will now be described.

In starting position, with no dose dispensed, an index element 14, for example indicating that the prime dose is still available, like letter "P", is visible in indication position through window 33 in drive member 31 from the outside, FIG. 14A.

Window 33 may be provided in activation part 64. Providing the window 33 in the drive member 31 is advantageous, because an index element can be easily recognized even during dose setting.

To set a dose a user grips the grip surfaces 66 of the drive member 31. The user then pulls the drive member 31 in a proximal direction away from the main housing part 2, FIG. 14B. Indicator 5 follows the movement of the drive member. Indicator 5 is prevented from rotating relative to the drive member 31 during this movement by a detent element 78, e.g. a detent spring (cf. FIG. 14). Indication surface 13 may extend along the outside of detent element 78. Indicator 5 may be retained in the activation part 64 of the drive member.

Alternatively the indicator may be rotated during movement of the indicator away from the proximal end 3, i.e. during setting, but is prevented from rotating during movement towards the proximal end 3, i.e. during dispense (not explicitly shown). However, rotation of the indicator during dose dispense is preferred over rotation of the indicator during dose setting, because the correct index element can be viewed by a user even after the next dose has already been set but has not yet been dispensed.

Detent element 78 may also prevent the indicator 5 from rotating under the influence of vibrations or impact loads. Detent element 78 is expediently configured to allow rotation of the indicator (only) if the rotation is caused by relative movement of piston rod and indicator with respect to one another.

Due to the slackness between threads 35 and 36, the piston rod is not moved during setting, i.e. threads 35 and 36 do not interact during setting.

The piston rod 6 is prevented from moving proximally by the part threads of the threaded circular opening 71 of the internal housing 56 interacting with thread features on the first thread 72 of the piston rod 6. As the drive member 31 travels in the proximal direction relative to the piston rod 6, the second thread 74 of the piston rod 6 is displaced radially inwards by the flank of the distal side of helical thread 77 of the drive member 31.

The proximal travel of the drive member 31 is limited by the guide slots (not shown) of the internal housing 56 to a distance corresponding to essentially one thread pitch of the helical thread 77 of the drive member 31. At the end of the travel of the drive member 31, the second thread 74 of the piston rod 6 engages with the helical thread 77 under the action of the flexible arms 75 of the piston rod 6.

As indicated in FIG. 14B, by this action the drive member 31 is displaced a distance essentially equal to one pitch of the helical thread 77 of the drive member 31 in the proximal direction relative to the piston rod 6. The action of the second thread 74 positively engaging the helical thread 77 of the drive member 31 under a force provided by the flexible arms 75 creates an audible and tactile feedback to the user to indicate that the dose has been set.

When the dose has been set, the user may then dispense this dose by depressing the dispensing face 67 of the activation part 64 of the drive member 31, i.e. by moving the drive member towards the proximal end 3, FIG. 14C. By this action the drive member 31 is moved axially in the distal direction relative to the main housing part 2. As the second thread 74 of the piston rod 6 is positively engaged with the helical thread 77 of the drive member 31 the piston rod 6 is caused to rotate with respect to the internal housing 56 by the axial movement of the drive member 31 in the distal direction. As the piston rod 6 rotates, the first thread 72 of the piston rod 6 rotates within the threaded circular opening 71 of the internal housing 56 causing the piston rod 6 to move axially in the distal direction with respect to the internal housing 56.

The distal axial movement of the piston rod 6 causes the pressure foot 73 to bear against the piston 54 of the cartridge 53 causing a dose of medicament to be dispensed through an attached needle.

Also, threads 35 and 36 interact with one another, thereby causing indicator 5 to rotate. Thread 36 can engage thread 35. The coupling between piston rod 6 and rotation member 7 causes the indicator to rotate the next index element 14 in line, e.g. digit "7" in FIG. 14C, into the indication position. The indicator 5 is adapted to count down the number of doses remaining for dispense. Indicator 5 rotates less than piston rod 6.

If the amount of the dose to be dispensed requires a rotation of the indicator by 120°, the indication surface may be rotated by 30° per dose delivered.

The distal travel of the drive member 31 is limited by the guide slots (not shown) of the internal housing 56. Audible and tactile feedback to indicate that the dose has been dispensed is provided by the interaction of an (additional) detent (not shown) of the drive member 31 with the pawl means (not shown) of the internal housing 56.

Further doses may be delivered as required up to a predetermined maximum number of doses. FIGS. 14D and 14E show the setting of the last dose and the dispensing of the last dose from the drug delivery device 50. The mechanism corresponds to the one described above in connection with FIGS. 14A to 14C. The index elements 14 on indication surface 13 rotate one after the other into indication position and preferably count down, e.g. to "0", as dose dispensing proceeds. Piston rod 6 advances forward as further doses are dispensed.

FIG. 14E shows the drug delivery device in a condition where the maximum number of doses has been delivered. In this condition lug features (not explicitly shown) on the piston rod 6 may interlock with lug features (not explicitly shown) on the drive member 31 to prevent further axial movement of the drive member 31 in the proximal direction.

Of course, other embodiments of the drive assembly as described above may be implemented in a drug delivery device according to this embodiment.

As the piston rod 6 moves translational and rotational, drive assemblies as described in connection with FIGS. 5 to 12 are particularly suitable to be implemented in a drug delivery device according to this embodiment.

The invention claimed is:

1. A drive assembly for use in a drug delivery device, the drive assembly comprising:
a housing having a proximal end and a distal end;
an axis extending between the proximal end and the distal end;
at least one drive member;
a piston rod adapted to be driven along the axis by the drive member; and
an indicator adapted to provide positional information about a position of the piston rod relative to the proximal end,
wherein
the indicator and the piston rod are configured to convert movement of the piston rod with respect to the housing into a rotational movement of the indicator, and the indicator comprises a rotation member configured to convert movement of the piston rod into the rotational movement of the indicator with the indicator being coupleable to the piston rod via the rotation member and wherein at least a part of the rotation member is arranged within the piston rod, characterized in that the rotation member runs from outside of the piston rod to inside of the piston rod through an opening of the piston rod, the opening being provided on that side of the piston rod that faces the proximal end.

2. The drive assembly according to claim 1, wherein the drive assembly is configured to move the piston rod unidirectionally along the axis.

3. The drive assembly according to claim 1, wherein the indicator has an indication surface that is provided with a plurality of index elements, the drive assembly being configured for at least one of the index elements to be visible from outside of the drive assembly.

4. The drive assembly according to claim 1, wherein the drive member is movable along the axis with respect to the housing and the indicator is coupled to the drive member with the indicator following an axial movement of the drive member.

5. The drive assembly according to claim 1, wherein the drive assembly is configured to restrict or prevent distal movement of the indicator along the axis with respect to the housing or with respect to the drive member.

6. The drive assembly according to claim 1, wherein one of the rotation member and the piston rod has a protrusion that is configured to mechanically interact with the other one of the rotation member and the piston rod for converting the movement of the piston rod into rotational movement of the rotation member.

7. The drive assembly according to claim 6, wherein the respective protrusion comprises one of a male thread, a knob, a rib, a lug or a pin.

8. The drive assembly according to claim 6, wherein both of the rotation member and the piston rod have a protrusion with the protrusions being configured to mechanically interact.

9. The drive assembly according to claim 6, wherein the protrusion engages the indentation.

10. The drive assembly according to claim 1, wherein at least one of the rotation member and the piston rod has an indentation that is configured to mechanically interact with the other one of the rotation member and the piston rod for converting the movement of the piston rod into rotational movement of the rotation member.

11. The drive assembly according to claim 10, wherein the indentation comprises one of a slit and a female thread.

12. The drive assembly according to claim 1, wherein the rotation member has a section which is configured to threadedly engage the piston rod.

13. The drive assembly according to claim 1, wherein the drive assembly is configured to move the piston rod distally along the axis and to rotate the piston rod.

14. The drive assembly according to claim 1, wherein the indicator is coupleable to the piston rod with a coupling being configured to convert rotational movement of the piston rod into rotational movement of the indicator of equal rotation angles.

15. The drive assembly according to claim 1, wherein the indicator is coupleable to the piston rod with a coupling being configured to convert rotational movement of the piston rod into rotational movement of the indicator of different rotation angles.

16. The drive assembly according to claim 1, wherein the drive assembly is configured to restrict or prevent rotational movement of the piston rod.

17. The drive assembly according to claim 1, wherein the drive assembly is configured to convert a distal movement of the piston rod along the axis into rotational movement of the indicator.

18. A drug delivery device according to claim 1 comprising a plurality of doses of a drug.

19. The drug delivery device according to claim 18, wherein the drive assembly is configured for the indicator to rotate when a dose is dispensed from the drug delivery device.

* * * * *